(12) United States Patent
Albert et al.

(10) Patent No.: US 7,825,260 B2
(45) Date of Patent: Nov. 2, 2010

(54) AMINOPROPANOL DERIVATIVES AS SPHINGOSINE-1-PHOSPHATE RECEPTOR MODULATORS

(75) Inventors: Rainer Albert, Basel (CH); Claus Ehrhardt, Lörrach (DE); Peter Ettmayer, Vienna (AT); Klaus Hinterding, Wittlingen (DE); Klemens Högenauer, Vienna (AT); Peter Nussbaumer, Maria Enzersdorf (AT)

(73) Assignee: Novartis AG, Basel (CH)

( * ) Notice: Subject to any disclaimer, the term of this patent is extended or adjusted under 35 U.S.C. 154(b) by 1347 days.

(21) Appl. No.: 10/554,557

(22) PCT Filed: Apr. 29, 2004

(86) PCT No.: PCT/EP2004/004572

§ 371 (c)(1),
(2), (4) Date: Dec. 22, 2005

(87) PCT Pub. No.: WO2004/096757

PCT Pub. Date: Nov. 11, 2004

(65) Prior Publication Data

US 2006/0211656 A1  Sep. 21, 2006

(30) Foreign Application Priority Data

Apr. 30, 2003 (GB) ................... 0309946.2
Dec. 19, 2003 (GB) ................... 0329494.9
Dec. 19, 2003 (GB) ................... 0329501.1

(51) Int. Cl.
*C07D 231/56* (2006.01)
*C07D 307/00* (2006.01)
*C07D 307/87* (2006.01)
*C09B 5/00* (2006.01)

(52) U.S. Cl. .................. 548/361.1; 548/416; 549/434; 549/462

(58) Field of Classification Search ................ 549/462, 549/434; 548/361.1, 416
See application file for complete search history.

(56) References Cited

U.S. PATENT DOCUMENTS

2007/0135501 A1*  6/2007  Hinterding et al. .......... 514/375
2007/0225260 A1*  9/2007  Hinterding et al. .......... 514/114

FOREIGN PATENT DOCUMENTS

| EP | 1 310 488 | 5/2003 |
| JP | 2002-316985 | * 10/2002 |
| WO | 02/076995 | 10/2002 |

OTHER PUBLICATIONS

Machine Translation of JP2002-316985.*
Database Chemabs, Nishi et al., "Immunosuppressant Benzothiophene Derivatives", Database Accession No. 137:337773 and JP 2002 316985, Oct. 31, 2002—Abstract.

* cited by examiner

*Primary Examiner*—Frederick Krass
*Assistant Examiner*—Sean Basquill
(74) *Attorney, Agent, or Firm*—Hoxie & Associates LLC

(57) ABSTRACT

Compounds of formula I,

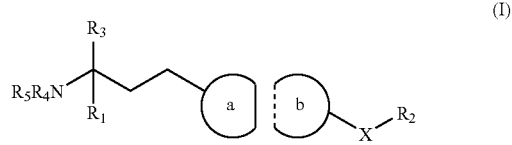

(I)

wherein X, a, b, $R_1$, $R_2$, $R_3$, $R_4$ and $R_5$ are as defined in the specification, processes for their production, their uses and pharmaceutical compositions containing them.

10 Claims, No Drawings

AMINOPROPANOL DERIVATIVES AS SPHINGOSINE-1-PHOSPHATE RECEPTOR MODULATORS

The present invention relates to amino-propanol derivatives, process for their production, their uses and pharmaceutical compositions containing them.

More particularly, the invention provides a compound of formula I

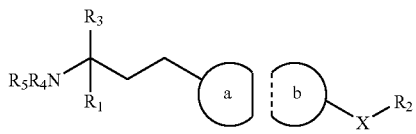

wherein
$R_1$ is $C_{1-6}$alkyl; $C_{1-6}$alkyl substituted by hydroxy, $C_{1-2}$alkoxy, or 1 to 6 fluorine atoms; $C_{2-6}$alkenyl; or $C_{2-6}$alkynyl;

X is O, $CH_2$, C=O or direct bond;

$R_2$ is optionally substituted $C_{1-7}$alkyl, optionally substituted $C_{1-7}$alkenyl, optionally substituted $C_{1-7}$alkinyl, optionally substituted $C_{3-6}$cycloalkyl, optionally substituted phenyl, or optionally substituted heteroaryl,
   wherein the substituted $C_{1-7}$alkyl, $C_{1-7}$alkenyl, $C_{1-7}$alkinyl or $C_{3-6}$cycloalkyl has 1 to 5 substituents selected from hydroxy, halogen, $C_{1-4}$alkyl, $C_{1-4}$alkoxy, $C_{1-4}$alkoxy substituted by 1 to 5 halogen atoms, $C_{3-6}$cycloalkyl, $C_{3-6}$cycloalkoxy, $C_{3-6}$cycloalkyl$C_{1-5}$alkyl, $C_{3-6}$cycloalkoxy$C_{1-5}$alkyl, cyano, optionally substituted phenyl, optionally substituted phenyloxy, optionally substituted heteroaryl, optionally substituted heteroaryloxy, optionally substituted heterocyclic residue optionally attached via oxygen;
   and wherein each of phenyl, phenyloxy, heteroaryl, heteroaryloxy, heterocyclic residue optionally attached via oxygen, independently may be substituted with 1 to 5 substituents selected from hydroxy, halogen, $C_{1-4}$alkyl, $C_{1-4}$alkyl substituted by 1 to 5 fluorine atoms, $C_{1-4}$alkoxy, $C_{1-4}$alkoxy substituted by 1 to 5 fluorine atoms, cyano, phenyl, and phenyl substituted by 1 to 5 substituents selected from hydroxy, halogen, $C_{1-4}$alkyl, $C_{1-4}$alkyl substituted by 1 to 5 fluorine atoms, $C_{1-4}$alkoxy, $C_{1-4}$alkoxy substituted by 1 to 5 fluorine atoms, and cyano; or each of phenyl, phenyloxy, heteroaryl, heteroaryloxy, heterocyclic residue optionally attached via oxygen independently may be fused to a heterocyclic residue;

$R_3$ is Z—$X_2$ wherein Z is $CH_2$, CHF or $CF_2$ and $X_2$ is OH or a residue of formula (a)

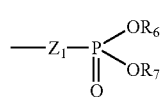

wherein $Z_1$ is a direct bond, $CH_2$, CHF, $CF_2$ or O, and each of $R_6$ and $R_7$, independently, is H, $C_{1-4}$alkyl optionally substituted by 1, 2 or 3 halogen atoms, or benzyl; and each of $R_4$ and $R_5$, independently, is H, $C_{1-4}$alkyl optionally substituted by 1, 2 or 3 halogen atoms, or acyl;

each of anellated rings a and b is independently $C_{5-6}$cycloalkyl, aryl, a heterocyclic residue, or heteroaryl;

in free form or in salt form.

Alkyl or alkyl moiety may be straight or branched chain. When alkyl is substituted by hydroxy it is preferably on the terminal carbon atom. Alkenyl may be e.g. vinyl. Alkynyl may be e.g. propyn-2-yl. Acyl may be a residue R—CO wherein R is $C_{1-6}$alkyl, $C_{3-6}$cycloalkyl, phenyl or phenyl$C_{1-4}$alkyl. Halogen may be fluorine, chlorine or bromine, preferably fluorine or chlorine.

Aryl may be phenyl, or naphthyl.

Heteroaryl may be a 5 to 8 membered aromatic ring comprising 1 to 4 heteroatoms selected from N, O and S, e.g. pyridyl, pyrimidinyl, pyrazinyl, furyl, oxazolyl, isoxazolyl, thienyl, thiazolyl, isothiazolyl, pyrrolyl, imidazolyl, or pyrazolyl.

By heterocyclic residue is meant a 3 to 8, preferably 5 to 8, membered saturated or unsaturated heterocyclic ring comprising 1 to 4 heteroatoms selected from N, O and S, e.g. tetrahydrofuryl, tetrahydropyranyl, aziridinyl, piperidinyl, pyrrolidinyl, piperazinyl.

Examples of annelated rings a and b are e.g. naphthyl; benzoxazoyl; benzothiazyl; benzofuryl; indolyl; indazolyl; or N-substituted-indazolyl, e.g. N—$C_{1-4}$alkyl-indazoyl, or e.g. N-aryl-indazolyl, wherein aryl is optionally substituted aryl e.g. benzyl, or benzyl optionally substituted by e.g. methoxy or nitro.

Compounds of formula I may exist in free form or in salt form, e.g. addition salts with e.g. inorganic acids, such as hydrochloride, hydrobromide or sulfate, salts with organic acids, such as acetate, fumarate, maleate, benzoate, citrate, malate, methanesulfonate or benzenesulfonate salts. Compounds of formula I and their salts, in hydrate or solvate form are also part of the invention.

When the compounds of formula I have asymmetric centers in the molecule, various optical isomers are obtained. The present invention also encompasses enantiomers, racemates, diastereoisomers and mixtures thereof. For example, the central carbon atom bearing $R_1$, $R_3$ and $NR_4R_5$ may have the R or S configuration. Compounds having the following 3-dimensional configuration are generally preferred:

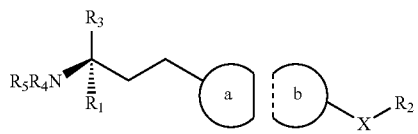

Moreover, when the compounds of formula I include geometric isomers, the present invention embraces cis-compounds, trans-compounds and mixtures thereof. Similar considerations apply in relation to starting materials exhibiting asymmetric carbon atoms or unsaturated bonds as mentioned above, e.g. compounds of formula II, III or IV as indicated below.

In the compounds of formula I, the following significances are preferred individually or in any sub-combination:
1. X is O or direct bond;
2. $R_1$ is $CH_3$ or $CH_2$—OH;
3. $R_2$ is $C_{1-7}$alkyl, substituted $C_{1-7}$alkyl, substituted phenyl, phenylalkyl, substituted phenylalkyl, biphenyl, substituted biphenyl, heteroaryl, or substituted heteroaryl,
   e.g. $C_{3-7}$ alkyl or $C_{3-7}$ alkyl substituted by 1 to 5 fluorine atoms;
   e.g. phenyl or substituted phenyl, e.g., phenyl substituted by hydroxy, substituted $C_{1-4}$alkyl, e.g. trifluormethyl, $C_{1-4}$alkoxy, halogen or cyano;

e.g. biphenyl or substituted biphenyl, e.g. biphenyl substituted with $C_{1-4}$-alkyl, substituted $C_{1-4}$alkyl, e.g. trifluormethyl, $C_{1-4}$alkoxy, halogen or cyano;

e.g. heteroaryl substituted by substituted $C_{1-4}$alkyl, e.g. trifluormethyl, cyano, or phenyl, e.g. thienyl substituted by phenyl or furyl substituted by phenyl;

4. $R_3$ is $CH_2$—OH or $CH_2OPO_3H_2$;
5. each of $R_4$ and $R_5$ is hydrogen;
6. a and b independently are aryl or heteroaryl, preferably a and b together form 2,6- or 2,7-disubstituted naphthyl, 2,5- or 2,6-disubstituted benzoxazolyl, 2,5- or 2,6-disubstituted benzothienyl, 2,5- or 2,6-disubstituted benzofuryl, 1,4- or 1,5-disubstituted indolyl, 3,6-indazolyl, or 3,6-N-substituted-indazolyl, e.g. 3,6-N-methyl-indazolyl.

The present invention also includes a process for the preparation of a compound of formula I which process comprises a) for a compound of formula I wherein $R_3$ is $Z$—$X_2$, $X_2$ being OH or a residue of formula (a), removing the protecting group present in a compound of formula II

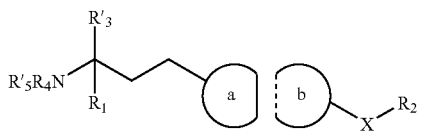

wherein X, $R_1$, $R_2$ and $R_4$ are as defined above, $R'_3$ is $Z$—$X_2$ wherein $X_2$ is OH and $R'_5$ is an amino protecting group, or b) for a compound of formula I wherein $R_3$ is $Z$—$X_2$, $X_2$ being a residue of formula (a) wherein $R_6$ and $R_7$ are H, removing the protecting groups present in a compound of formula III

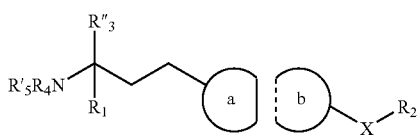

wherein X, $R_1$, $R_2$, $R_4$ and $R'_5$ are as defined above, and $R''_3$ is $Z$—$X_2$ wherein $X_2$ is a residue of formula (a')

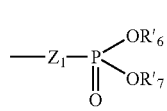

wherein $Z_1$ is as defined above and each of $R'_6$ or $R'_7$ is a hydrolysable or hydrogenolysable group or $R'_6$ and $R'_7$ form together a divalent bridging residue optionally fused to a ring (e.g. benzene ring), and, where required, converting the compounds of formula I obtained in free form into the desired salt form, or vice versa.

Process step a) may be carried out in accordance with methods known in the art. The removal of the amino protecting groups may conveniently be performed according to methods known in the art, e.g. by hydrolysis, e.g. in an acidic medium, for example using hydrochloric acid. Examples of protecting groups for amino groups are e.g. as disclosed in "Protective Groups in Organic Synthesis" T. W. Greene, J. Wiley & Sons NY, $2^{nd}$ ed., chapter 7, 1991, and references therein, e.g. benzyl, p-methoxybenzyl, methoxymethyl, tetrahydropyranyl, trialkylsilyl, acyl, tert.-butoxy-carbonyl, benzyloxycarbonyl, 9-fluorenyl methoxy carbonyl, trifluoroacetyl, and the like.

In the residue of formula (a'), each of $R'_6$ and $R'_7$ may have the significance of e.g. alkyl, e.g. tert-butyl; phenyl or benzyl or form together a cyclic system such as in 1,5-dihydro-2,4,3-benzodioxaphosphepin.

Process step (b) may be performed according to methods known in the art, e.g. by hydrolysis, e.g. in a basic medium when $R'_6$ and $R'_7$ are each a hydrolysable group, for example using a hydroxide such as barium hydroxide, or in an acidic medium when $R'_6$ and $R'_7$ are each a tert-butyl group. It may also be performed by hydrogenolysis, e.g. in the presence of a catalyst, e.g. Pd/C, followed by hydrolysis, e.g. in an acidic medium, for example HCl. Compounds of formulae V and VI, used as starting materials, and salts thereof are also novel and form part of the invention.

The present invention also includes a process for the preparation of a compound of formula II wherein X is O which process comprises alkylating a compound of formula IV

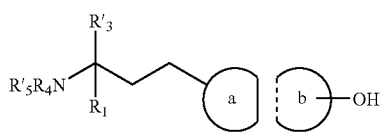

wherein $R_1$, $R'_3$, $R_4$ and $R'_5$ are as defined above, to introduce the desired residue -$R_2$ by an alkylation. Alkylation of the compounds of formula IV may be performed according to methods known in the art, e.g. by nucleophilic substitution, e.g. by reaction with an alkylating agent $R_2$—$X_3$ wherein $X_3$ is mesylate, tosylate, triflate, nosylate or an halogen, e.g. chloride, bromide or iodide. The alkylation may also be carried out by following the Mitsunobu protocol using $R_2$—OH (e.g. as disclosed in Hughes, Organic Preparations and Procedures International 28, 127-64, 1996 or D. L. Hughes, Org. React. 42, 335, 1992), in solution or on solid phase support synthesis, e.g. by attaching the compound of formula IV to a resin. Alternatively, either triphenylphosphine or e.g. diethyl azocarboxylate bound to a resin, e.g. polystyrene, can be used.

Insofar as the production of the starting materials is not particularly described, the compounds are known or may be prepared analogously to methods known in the art or as disclosed in the Examples hereinafter.

The following Examples are illustrative of the Invention. Melting points (Mp) are uncorrected.

| | |
|---|---|
| RT = | room temperature |
| THF = | tetrahydrofuran |
| AcOEt = | ethyl acetate |
| DCM = | dichloromethane |

EXAMPLE 1

(R)-2-amino-2-methyl-4-(6-pentyloxynaphthalen-2-yl)butan-1-ol

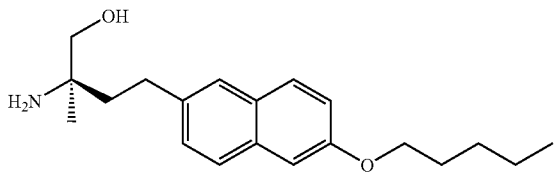

N-Boc-(R)-2-amino-2-methyl-4-(6-pentyloxynaphthalen-2-yl)butan-1-ol (21 mg, 0.05 mmol) is dissolved in methanolic hydrochloric acid solution and stirred for 2 hours at RT. The solvent is distilled off in vacuo, and the residue is dried to obtain the title compound as its hydrochloride salt. NMR (CDCl$_3$/d$_6$DMSO=2/1) δ 7.65 (d, J=8.5 Hz, 1H), 7.63 (d, J=8.1 Hz, 1H), 7.57 (s, 1H), 7.32 (d, J=8.3 Hz, 1H), 7.07-7.17 (m, 2H), 4.06 (t, J=6.7 Hz, 2H), 3.71 (s, 2H), 2.78-2.88 (m, 2H), 2.0-2.1 (m, 2H), 1.8-1.9 (m, 2H), 1.38-1.53 (m, 4H), 1.41 (s, 3H), 0.95 (t, J=7 Hz, 3H). ESI+ MS: m/z=316.5 (MH)$^+$.

N-Boc-(R)-2-amino-2-methyl-4-(6-pentyloxynaphthalen-2-yl)butan-1-ol may be synthesized as follows:

A mixture of N-Boc protected (R)-2-amino-2-methyl-4-(6-hydroxynaphthalen-2-yl)butan-1-ol (485 mg, 1.17 mmol), potassium carbonate (300 mg, 2.17 mmol), 1-iodopentane (184 µl, 1.2 mmol), and acetone (6 ml) is heated to reflux overnight. The solvent is distilled off, and the residue is partitioned between water and AcOEt. The organic layer is dried over sodium sulfate and concentrated in vacuo. Chromatography on silica gel (cyclohexane/AcOEt=2/1) gives pure title compound as colorless oil. NMR (CDCl$_3$) δ 7.65 (d, J=8.8 Hz, 1H), 7.64 (d, J=8.3 Hz, 1H), 7.55 (s, 1H), 7.29 (dd, J=1.6+8.3 Hz, 1H), 7.12 (dd, J=7.09 (d, J=2.5 Hz, 1H), 4.65 (s, 1H), 4.06 (t, J=6.6 Hz, 2H), 3.74 (d, J=11.5 Hz, 1H), 3.67 (d, J=11.5 Hz, 1H), 2.67-2.86 (m, 2H), 2.08-2.18 (m, 1H), 1.9-2.01 (m, 1H) 2H), 1.36-1.55 (m, 4H), 1.43 (s, 9H), 1.26 (s, 3H), 0.95 (t, J=7.2 Hz, 3H). $^1$H NMR (CDCl$_3$/d$_8$DMSO=2/1): 7.65 (d, J=8.5 Hz, 1H), 7.63 (d, J=8.1 Hz, 1H), 7.57 (s, 1H), 7.32 (d, J=8.3 Hz, 1H), 7.07-7.17 (m, 2H), 4.06 (t, J=6.7 Hz, 2H), 3.71 (s, 2H), 2.78-2.88 (m, 2H), 2.0-2.1 (m, 2H), 1.8-1.9 (m, 2H), 1.38-1.53 (m, 4H), 1.41 (s, 3H), 0.95 (t, J=7 Hz, 3H).

EXAMPLES 2 TO 9

The examples shown in Table 1 are prepared as described in example 1.

TABLE 1 wherein R'

| Ex. | R' | $^1$H-NMR in d$_6$DMSO if not indicated otherwise |
|---|---|---|
| 2 | —CH$_2$CH$_2$CH$_2$CH$_2$CH$_2$CH$_2$CH$_3$ | 7.8 (d, J = 8.6 Hz, 2H), 7.67 (s, 1H), 7.39 (dd, J = 8.3 + 1.5 Hz, 1H), 7.33 (d, J = 2.4 Hz, 1H), 7.19 (dd, J = 8.9 + 2.4 Hz, 1H), 5.58 (br.s, 1H), 4.12 (t, J = 6.5 Hz, 2H), 3.45-3.6 (m, 2H), 2.79 (t, J = 8.7 Hz, 2H), 1.78-1.99 (m, 4H), 1.3-1.56 (m, 8H), 1.29 (s, 3H), 0.94 (t, J = 7 Hz, 3H) |
| 3 | —CH$_2$CH$_2$CH$_2$CH(CH$_3$)$_2$ | 7.78 (d, J = 8.7 Hz, 2H), 7.65 (s, 1H), 7.37 (dd, J = 8.3 + 1.4 Hz, 1H), 7.31 (d, J = 2.3 Hz, 1H), 7.17 (dd, J = 8.9 + 2.3 Hz, 1H), 5.55 (br.s, 1H), 4.10 (t, J = 6.5 Hz, 2H), 3.42-3.6 (m, 2H), 2.77 (t, J = 8.7 Hz, 2H), 1.76-1.99 (m, 4H), 1.65 (hept, J = 6.6 Hz, 1H), 1.34-1.43 (m, 2H), 1.28 (s, 3H), 0.94 (t, J = 6.6 Hz, 6H) |
| 4 | —CH$_2$CH$_2$CH$_3$ | 7.77 (d, J = 9.4 Hz, 1H), 7.74 (d, J = 9.3 Hz, 1H), 7.63 (s, 1H), 7.35 (dd, J = 8.3 + 1.5 Hz, 1H), 7.28 (d, J = 2.4 Hz, 1H), 7.15 (dd, J = 8.9 + 2.4 Hz, 1H), 4.60 (br.s, 1H), 4.06 (t, J = 6.5 Hz, 2H), 3.23 (s, 2H), 2.65-2.84 (m, 2H), 1.82 (sex, J = 7.2 Hz, 2H), 1.59-1.68 (m, 2H), 1.06 (t, J = 7.2 Hz, 6H), 1.03 (s, 3H) |
| 5 | —CH$_2$CH$_2$CH$_2$CH$_3$ | 7.93 (br s, residual NH$_3^+$ signal) 7.67-7.61 (m, 2H), 7.53 (s, 1H), 7.26-7.22 (m, 1H), 7.11 (dd, J = 9 Hz, 2 Hz, 1H), 7.08-7.06 (m, 1H), 4.05 (t, J = 7 Hz, 2H), 3.67 (d, J = 12 Hz, 1H), 3.59 (d, J = 12 Hz, 1H), 2.82-2.73 (m, 2H), 2.05-1.93 (m, 2H), 1.85-1.77 (m, 2H), 1.55-1.48 (m, 2H), 0.98 (t, J = 7 Hz, 3H) in CDCl$_3$/d$_4$-MeOH = 30/1 |
| 6 | —CH$_2$CH$_2$CH$_2$CF$_2$CF$_3$ | 7.83 (br s, 3H), 7.73-7.71 (m, 2H), 7.62 (s, 1H), 7.32 (dd, J = 8 Hz, 2 Hz, 1H), 7.30 (d, J = 2 Hz, 1H), 7.13 (dd, J = 9 Hz, 2 Hz, 1H), 5.50 (t, J = 5 Hz, 1H), 4.15 (t, J = 14 Hz, 2H), 3.51-3.38 (m, 2H), 2.75-2.57 (m, 2H), 2.48-2.30 (m, 2H), 2.08-1.98 (m, 2H), 1.90-1.78 (m, 2H), 1.22 (s, 3H) |
| 7 | —CH$_2$-cyclopropyl | 7.78 (br.s, 3H), 7.72 (d, J = 8.7 Hz, 1H), 7.70 (d, J = 7 Hz, 1H), 7.59 (s, 1H), 7.31 (dd, J = 8.4 + 1.6 Hz, 1H), 7.22 (d, J = 2.4 Hz, 1H), 7.13 (dd, J = 8.9 + 2.4 Hz, 1H), 5.49 (br.s, 1H), 3.89 (d, J = 7 Hz, 2H), 3.37-3.53 (m, 2H), 2.71 (t, J = 8.8 Hz, 2H), 1.77-1.94 (m, 2H), 1.21-1.34 (m, 1H), 1.23 (s, 3H), 0.55-0.63 (m, 2H), 0.32-0.38 (m, 2H) |

TABLE 1-continued

| Ex. | wherein R' | ¹H-NMR in d₆DMSO if not indicated otherwise |
|---|---|---|
| 8 | —CH₂CH₂CH₂CF₃ | 7.88 (br.s., 3H), 7.75 (d, J = 8.9 Hz, 2H), 7.74 (d, J = 8.4 Hz, 1H), 7.61 (s, 1H), 7.33 (dd, J = 8.4 + 1.5 Hz, 1H), 7.27 (d, J = 2.4 Hz, 1H), 7.14 (dd, J = 8.9 + 2.5 Hz, 1H), 5.51 (t, J = 3.9 Hz, 1H), 4.13 (t, J = 6.2 Hz, 2H), 3.39-3.54 (m, 2H), 2.72 (t, J = 8.7 Hz, 2H), 2.38-2.53 (m, 2H), 1.78-2.04 (m, 4H), 1.23 (s, 3H) |
| 9 | —CH₂-cyclohexyl | 7.83 (br.s., 3H), 7.73 (d, J = 8.3 Hz, 1H), 7.72 (d, J = 8.9 Hz, 1H), 7.59 (s, 1H), 7.31 (dd, J = 8.4 + 1.6 Hz, 1H), 7.25 (d, J = 2.4 Hz, 1H), 7.12 (dd, J = 8.9 + 2.4 Hz, 1H), 5.51 (t, J = 5 Hz, 1H), 3.86 (d, J = 6.3 Hz, 2H), 3.38-3.54 (m, 2H), 2.71 (t, J = 8.7 Hz, 2H), 1.62-1.94 (m, 8H), 1.02-1.32 (m, 5H), 1.22 (s, 3H) |

EXAMPLE 10

2-Amino-2-[2-(6-pentyloxy-naphthalen-2-yl)-ethyl]-propane-1,3-diol

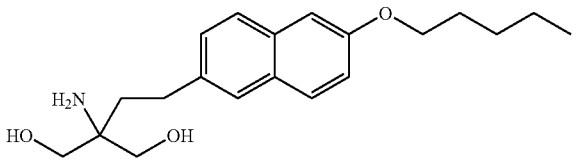

2,2-di(hydroxymethyl)-3-(6-pentyloxynaphthalene-2-yl)-propargylamine (53 mg, 0.12 mmol) was dissolved in AcOEt, charged with palladium on charcoal (10 mg) and hydrogen and stirred for 5 h under an atmosphere of hydrogen. The mixture was filtered over Celite, and the solvent was distilled off to give the pure title compound. ¹H NMR (d₆DMSO, free base): 7.70 (d, J=9.2 Hz, 1H), 7.68 (d, J=9.9 Hz, 1H), 7.33 (s, 1H), 7.29 (dd, J=8.4+1.6 Hz, 1H), 7.22 (d, J=2.4 Hz, 1H), 7.08 (dd, J=8.9+2.5 Hz, 1H), 4.44 (t, J=5 Hz, 1H), 4.04 (t, J=6.6 Hz, 2H), 3.28-3.35 (m, 4H), 2.67-2.73 (m, 2H), 1.7-1.8 (m, 2H), 1.52-1.6 (m, 2H), 1.3-1.48 (m, 4H), 0.89 (t, J=7.1 Hz, 3H).

2,2-di(hydroxymethyl)-3-(6-pentyloxynaphthalene-2-yl)-propargylamine may be synthesized as follows:

N-acetyl-2,2-di(acetoxymethyl)-3-(6-pentyloxynaphthalene-2-yl)propargylamine (33 mg, 0.07 mmol) was dissolved in methanol and treated with excess of 1N NaOH. The mixture was heated to reflux for 5 h and then acidified with 1N HCl. The precipitated hydrochloride salt was collected by filtration and obtained in pure form after washing with water. The free base may be obtained by treatment with base and extraction with AcOEt. Mp (HCl) 199° C., decomposition; mp (free base) 144-147° C.

N-acetyl-2,2-di(acetoxymethyl)-3-(6-pentyloxynaphthalene-2-yl)-propargylamine may be synthesized as follows:

2-Bromo-6-pentyloxynaphthalene (84 mg, 0.3 mmol), N-acetyl-2,2-di(acetoxymethyl)-propargylamine (69 mg, 0.3 mmol), tetrakis-triphenylphosphine palladium (17 mg, 0.01 mmol), coprous iodide (5 mg, 0.03 mmol), and triethylamine (0.12 µl) were mixed in dry DMF (1 ml) and heated to 100° C. over night under argon atmosphere. After cooling the mixture was partitioned between water and AcOEt, and the organic layer was washed with brine, dried over magnesium sulfate and evaporated. Purification by silica gel chromatography (cyclohexane/AcOEt=2/3) yielded pure title compound, mp 106-109° C.

EXAMPLE 11

2-Amino-2-[2-(4-heptyloxy-naphthalen-1-yl)ethyl]-propane-1,3-diol

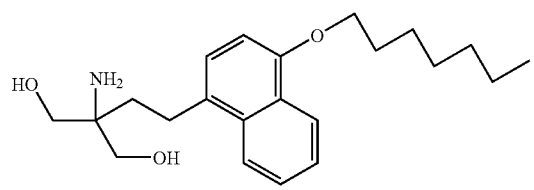

The title compound was prepared as described In Example 10 using the appropriate starting materials. ¹H NMR (CDCl₃, free base): 8.33 (d, J=8.2 Hz, 1H), 7.96 (d, J=8.5 Hz, 1H), 7.43-7.56 (m, 2H), 7.21 (d, J=7.8 Hz, 1H), 6.71 (d, J=7.8 Hz, 1H), 4.1 (t, J=6.4 Hz, 2H), 3.69 (d, J=10.6 Hz, 2H), 3.6 (d, J=10.6 Hz, 2H), 2.98-3.07 (m, 2H), 1.78-1.96 (m, 4H), 1.5-1.62 (m, 2H), 1.35-1.46 (m, 6H), 0.9 (t, J=7 Hz, 3H).

EXAMPLE 12

Phosphoric acid mono-[(R)-2-amino-2-methyl-4-(6-pentyloxynaphthalen-2-yl)but-1-yl]ester

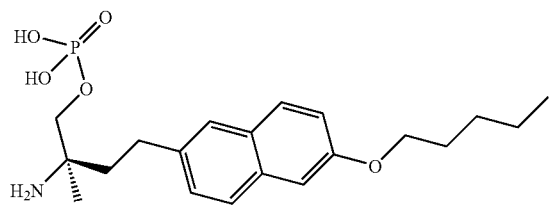

N-Boc protected (R)-2-amino-2-methyl-4-(6-pentyloxynaphthalen-2-yl)butan-1-ol (60 mg, 0.14 mmol) is dissolved in dry THF and treated with tetrazole (30 mg, 0.42 mmol) and di-t-butyl-N,N-diisopropylphosphoramide (78 mg, 0.28 mmol) at RT. The mixture is stirred overnight under argon, and then aqueous hydrogen peroxide solution (160 μl of a 30% solution in water, 1.4 mmol) is added. After an additional hour, the mixture is treated with excess aqueous sodium thiosulfate solution followed by extraction with AcOEt. The combined organic layers are washed with water and brine, dried over sodium sulfate and concentrated in vacuo. Chromatography on silica gel (cyclohexane/AcOEt=2/1) affords pure phosphoric acid di-t-butyl ester (R)-2-amino-2-methyl-4-(6-pentyloxynaphthalen-2-yl)but-1-yl ester: NMR (CDCl$_3$) δ 7.58 (d, J=8.7 Hz, 1H), 7.56 (d, J=8.4 Hz, 1H), 7.47 (s, 1H), 7.22 (dd, J=8.4+1.7 Hz, 1H), 6.99-7.06 (m, 2H), 4.79 (br, s, 1H), 4.02 (dd, J=10+5.5 Hz, 1H), 3.99 (t, J=6.6 Hz, 2H), 3.82 (dd, J=10+5.5 Hz, 1H), 2.6-2.72 (m, 2H), 2.04-2.17 (m, 1H), 1.88-1.98 (m, 1H), 1.72-1.83 (m, 2H), 1.43 (s, 18H), 1.37 (s, 9H), 1.28-1.45 (m, 4H), 1.31 (s, 3H), 0.88 (t, J=7.1 Hz). This intermediate (54 mg, 0.089 mmol) is stirred with saturated methanolic hydrochloric acid overnight at room temperature. The solvent is distilled off, and the residue is subject to purification by HPLC yielding phosphoric acid mono-[(R)-2-amino-2-methyl-4-(6-pentyloxynaphthalen-2-yl)but-1-yl] ester as colorless powder. Mp 266-267° C. $^1$H NMR (CD$_3$OD/DCl=10/1): 7.7 (d, J=9 Hz, 1H), 7.68 (d, J=9.3 Hz, 1H), 7.62 (s, 1H), 7.34 (dd, J=8.4+1.8 Hz, 1H), 7.17 (d, J=2.5 Hz, 1H), 7.1 (dd, J=9+2.5 Hz, 1H), 4.15 (dd, J=11.1+5.1 Hz, 1H), 4.11 (t, J=6.5 Hz, 2H), 4.04 (dd, J=11.1+4.6 Hz, 1H), 2.78-2.9 (m, 2H), 1.98-2.16 (m, 2H), 1.8-1.87 (m, 2H), 1.39-1.55 (m, 4H), 1.45 (s, 3H), 0.96 (t, J=7.2 Hz, 3H).

EXAMPLES 13 AND 14

The examples shown in Table 2 are prepared as described in example 12.

TABLE 2

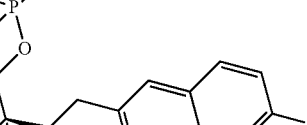

| Ex. | wherein R' | $^1$H-NMR and MS data |
|---|---|---|
| 13 | ![F-structure] | H-NMR (d$_6$-DMSO/DCl = 30/1): 7.74 (s, 1H), 7.71 (s, 1H), 7.61 (br s, 1H), 7.33 (dd, J = 2 Hz, 9 Hz, 1H), 7.27 (d, J = 3 Hz, 1H), 7.13 (dd, J = 3 Hz, 9 Hz, 1H), 4.14 (t, J = 6 Hz, 2H), 2.72 (m, 2H), 2.48-2.35 (m, 2H), 2.03-1.88 (m, 4H), 1.30 (s, 3H). MS (ESI+): 486.2 [M + H]$^+$ |
| 14 | ![CH3-structure] | $^1$H NMR (CD$_3$OD), selected signals: 7.17 (d, J = 2.6 Jz, 1H), 7.1 (dd, J = 2.6 + 9 Hz, 1H), 4.03 (t, J = 6.5 Hz, 2H), 1.78-1.84 (m, 2H), 1.47 (s, 3H), 1.08 (t, J = 7.5 Hz, 3H); MS-ESI$^+$: 368 [M + H]$^+$. |

EXAMPLE 15

(R)-2-Amino-2-methyl-4-(2-pentyl-benzoxazol-5-yl)-butan-1-ol

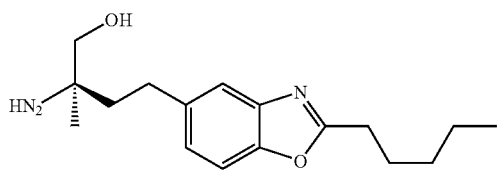

Method A:

A solution of [(R)-1-Hydroxymethyl-1-methyl-3-(2-pentyl-benzoxazol-5-yl)-propyl]-carbamic acid tert-butyl ester (31 mg, 0.079 mmol) in diethyl ether (2 ml) was treated with 2M HCl in diethyl ether and stirred for 2 hours at RT. The reaction was quenched by the addition of a solution of 28% aqueous ammonium hydroxide (2 ml), methanol (2 ml) and DCM (1 ml). After evaporation of the solvents in vacuum the residue was purified by silica gel chromatography (eluent: CH$_2$Cl$_2$/MeOH/28% NH$_4$OH: 9/1/0.1). Crystallization from n-pentane provided the title compound as a colorless solid. $^1$H NMR (DMSO-d6) δ: 7.52 (d, J=7.9 Hz; 1H), 7.45 (s; 1H), 7.15 (d, J=7.9 Hz; 1H), 3.30 (bs; 2H), 2.88 (bs; 2H), 2.77-2.55 (m; 2H), 1.78 (bs; 2H), 1.63 (bs; 2H), 1.32 (bs; 4H), 1.03 (s; 3H), 0.85 (bs; 3H).

Preparation of [(R)-1-Hydroxymethyl-1-methyl-3-(2-pentyl-benzoxazol-5-yl)-propyl]-carbamic acid tert-butyl ester A solution of [(R)-3-(3-Amino-4-hydroxy-phenyl)-1-hydroxymethyl-1-methyl-propyl]-carbamic acid tert-butyl ester (500 mg, 1.61 mmol) and hexanimidic acid ethyl ester hydrochloride (318 mg, 1.77 mmol) in DCM (6 ml) was stirred for 16 hours at RT. Evaporation of the solvent in vacuum was followed by silica gel chromatography (eluent: DCM/methanol 40/1). Product containing fractions were pooled and evaporated in vacuum. Crystallization from pentane provided the title compound as a colorless solid. mp: 92.7/92.6

Preparation of [(R)-3-(3-Amino-4-hydroxy-phenyl)-1-hydroxymethyl-1-methyl-propyl]-carbamic acid tert-butyl ester An argon purged solution of [(R)-1-Hydroxymethyl-3-(4-hydroxy-3-nitro-phenyl)-1-methyl-propyl]-carbamic acid tert-butyl ester (3.02 g, 8.87 mmol) in ethanol (40 ml) was treated with 10% Pd on activated charcoal (0.5 g). Argon was replaced by hydrogen and the reaction was allowed to proceed under atmospheric pressure for 2 hours. The reaction suspension was filtered and the filtrate evaporated to dryness in vacuum. Silica gel chromatography (eluent: DCM/methanol 20/1 to 10/1) followed by crystallization from diethyl ether provided the title compound as colorless crystals. mp 122.1/123.0° C.

Preparation of [(R)-1-Hydroxymethyl-3-(4-hydroxy-3-nitro-phenyl-1-methyl-propyl]-carbamic acid tert-butyl ester A solution of [(R)-1-Hydroxymethyl-3-(4-hydroxy-phenyl)-1-methyl-propyl]-carbamic acid tert-butyl ester (5.298 g, 17.936 mmol) in dry ethanol (27 ml) was treated with $Fe(NO_3)_3.9 H_2O$ (5.797 g, 14.348 mmol) and stirred for 2 hours at 40° C. while the color changed from a dark blue to a reddish brown. After cooling to RT the reaction mixture was distributed between 1N HCl (200 ml) and DCM (200 ml). The aqueous layer was washed two times with DCM and the combined organic layers were dried of $MgSO_4$ and concentrated in vacuum. Flash chromatography (eluent: DCM/methanol 40/1) provided the title compound as a yellowish amorphous solid. $^1$H-NMR (CDCl$_3$) δ: 10.45 (s; 1H), 7.92 (d, J=2.2 Hz; 1H), 7.45 (dd, J=2.2, 8.6 Hz; 1H), 7.09 (d, J=8.6 Hz; 1H), 3.68 (m; 2H), 2.73-2.52 (m; 2H), 2.10-1.8 (m; 2H), 1.45 (s; 9H), 1.23 (s; 3H).

Method B:

Sodium borohydride (262 mg, 6.925 mmol) was suspended in dry ethanol (7 ml), cooled to −10° C., treated with CaCl$_2$ (284 mg, 3.4625 mmol) and stirred for 45 minutes while warming to 0° C. A solution of (R)-2-Amino-2-methyl-4-(2-pentyl-benzoxazol-5-yl)-butyric acid methyl ester (147 mg, 0.462) in dry ethanol (2 ml) was added to the reaction slurry and stirred for 2 hours at 8-10° C. The precipitate was collected on a sinter funnel and washed with ethanol. The filtrate and the ethanol washings were combined and concentrated in vacuum. The residue was distributed between 1 N aqueous NaOH and chloroform. The organic layer was dried over MgSO$_4$ and concentrated in vacuum. Silica gel chromatography (eluent: CH$_2$Cl$_2$/MeOH/28% NH$_4$OH: 9/1/0.1) provided the title compound as an amorphous colorless solid.

Preparation of (R)-2-Amino-2-methyl-4-(2-pentyl-benzoxazol-5-yl)-butyric acid methyl ester A suspension of (R)-2-Amino-4-(3-hexanoylamino-4-hydroxy-phenyl)-2-methyl-butyric acid methyl ester trifluoro acetic acid salt (460 mg, 1.02 mmol) in dry toluene was heated under pressure (microwave Emrys optimizer) to 200° C. for 10 minutes. After cooling to RT the reaction mixture was distributed between AcOEt and a saturated aqueous NaHCO$_3$ solution. Silica gel chromatography (eluent CH$_2$Cl$_2$/MeOH 10/1) provided the title compound as an amorphous colorless solid. $^1$H-NMR (DMSO-d6): 7.51 (d, J=8.3 Hz; 1H), 7.42 (d, J=1.2 Hz; 1H), 7.12 (dd, J=8.3, 1.2 Hz; 1H), 3.60 (s; 3H), 2.88 (t, J=7.4 Hz; 2H), 2.71-2.63/2.58-2.50 (m; 2H), 1.92 (bs; 2H), 1.90-1.82/1.80-1.73 (m; 2H), 1.43-1.28 (m; 4H), 1.22 (s; 3H), 0.85 (m; 3H).

Preparation of (R)-2-Amino-4-(3-hexanoylamino-4-hydroxy-phenyl)-2-methyl-butyric acid methyl ester trifluoro acetic acid salt Under an argon atmosphere, a −70° C. solution of (S)-2-Isopropyl-3,6-dimethoxy-5-methyl-2,5-dihydro-pyrazine (652.5 µl, 3.291 mmol) in dry THF (7 ml) was treated with a solution of n-butyl lithium in n-hexane (2.1 ml of a 1.6M solution, 3.29 mmol). After stirring for 10 minutes a solution of 5-(2-iodo-ethyl)-2-pentyl-benzoxazole (753 mg, 2.19 mmol) in dry THF (5 ml) was added and the reaction mixture was stirred for 90 minutes at −65° C. followed by 2 hours at 0-5° C. The reaction was distributed between AcOEt and saturated aqueous ammonium chloride. The organic layer dried over MgSO$_4$ and concentrated in vacuum. Silica-gel flash chromatography (pentane/diethyl ether 4/1) provided the crude 5-[2-((2R,5S)-5-Isopropyl-3,6-dimethoxy-2-methyl-2,5-dihydro-pyrazin-2-yl)-ethyl]-2-pentyl-benzoxazole. The crude product was dissolved in acetonitrile (21 ml) and treated with water (21 ml) and trifluoroacetic acid (450 µl) and stirred for 3 days at RT. The solvents were removed in vacuum and the title compound was obtained after reversed phase chromatography (Waters, C-18, eluent: gradient of water/acetonitrile containing 0.1% trifluoroacetic acid) as an amorphous solid. $^1$H-NMR (CDCl$_3$) δ: 8.50 (s; 1H), 6.98 (s; 1H); 8.86/6.83 (2 broad singlets; 2H), 3.71 (s; 3H), 2.75-2.35 (m; 4H), 2.20 (broad s; 2H), 1.70 (broad s; 2H), 1.61 (s; 3H), 1.40-1.20 (m; 4H), 0.90 (m; 3H).

Preparation of 5-(2-Iodo-ethyl)-2-pentyl-benzoxazole

Under an argon atmosphere, a 0° C. solution of 2-(2-pentyl-benzoxazol-5-yl)-ethanol (1.63 g, 6.99 mmol) in dry THF (49 ml) was treated with triphenyl phosphine (2.018 b, 7.693 mmol) and imidazole (1.05 g, 15.38 mmol). After complete dissolution iodide (1.95 g, 7.69 mmol) was added in small portion so that the reaction temperature never exceeded 4° C. After stirring for 3 hours at 0° C. the reaction mixture was distributed between diethyl ether and saturated aqueous ammonium hydrochloride. The organic layer was evaporated in vacuum, suspended in diethyl ether, filtered and the filtrate concentrated in vacuum. Silica gel chromatography (eluent: pentane/diethyl ether 4/1) followed by crystallization from pentane provided the title compound as colorless crystals. mp: 47.7/48.7° C.

Preparation of 2-(2-pentyl-benzoxazol-5-yl)-ethanol

A solution of (2-pentyl-benzoxazol-5-yl)-acetic acid (2.11 g, 8.53 mmol) in triethyl orthoacetate (4.67 ml, 25.6 mmol) was heated under pressure (in three portions in the microwave Emrys optimizer) to 180° C. for 8 minutes. After cooling to RT the reaction mixture was distributed between AcOEt and saturated aqueous sodium hydrogen carbonate. The organic layer was washed two times with water, dried over MgSO4 and concentrated in vacuum. 1.88 g of the crude (2-pentyl-benzoxazol-5-yl)-acetic acid ethyl ester (2.31 g, 99%) were dissolved in dry ethanol (43 ml) and added to a solution of Ca(BH$_4$)$_2$ (prepared from sodium borohydride (3.87 g, 102.4 mmol) suspended in dry ethanol (130 ml), cooled to −10° C., treated with CaCl$_2$ (5.68 g, 51.2 mmol) and stirred for 45 minutes while warming to 0° C.). After stirring for 2 hours at 8° C. the reaction mixture was filtered and the precipitate washed with ethanol. The filtrate was combined with the washings and concentrated in vacuum, treated with MeOH and concentrated again. Silica gel chromatography (eluent: DCM/methanol 10/1) provided the title compound as colorless solid. $^1$H-NMR (DMSO-d6) δ: 7.51 (d, J=8.1 Hz; 1H), 7.49 (s; 1H), 7.16 (dd, J=8.3, 1.6 Hz; 1H), 4.60 (t, J=5.2 Hz; 1H), 3.61 (m; 2H), 2.88 (t, J=7.4 Hz; 2H), 2.80 (t, J=7.0 Hz; 2H), 1.76 (m; 2H), 1.30 (m; 4H), 0.85 (m; 3H).

Preparation of (2-pentyl-benzoxazol-5-yl)-acetic acid

A solution of (3-aminohydroxy-phenyl)-acetic acid (4.65 g, 27.8 mmol) in methanol (79 ml) was treated with hexanimidic acid ethyl ester hydrochloride (5.00 g, 27.8 mmol) and stirred for 14 hours at RT. The solvent was evaporated in vacuum and the residue purified by silica gel chromatography (eluent: DCM/methanol 10/1). Crystallization from Cyclohexane/n-pentane provided the title compound as colorless crystals. mp: 58.2/57.1° C.

EXAMPLE 16

(R)-2-Amino-2-methyl-4-(2-phenyl-benzoxazol-5-yl)-butan-1-ol

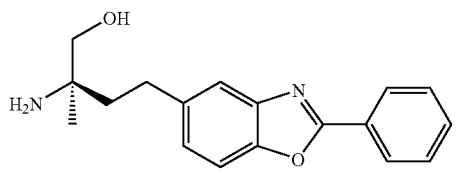

The title compound was prepared as a colorless solid as in Example 15 (Method A) using [(R)-1-hydroxymethyl-1-methyl-3-(2-phenyl-benzoxazol-5-yl)-propyl]-carbamic acid tert-butyl ester. mp. 127.9-128.1° C. $^1$H-NMR (DMSO-d6) δ: 8.18 (m; 2H), 7.66 (d, J=8.4 Hz; 1H), 7.60 (m; 3H), 7.52 (d, J=8.4 Hz; 1H), 4.57 (s; 1H), 3.15 (s; 2H), 2.72 (m; 2H), 1.58 (m; 2H), 0.97 (s; 3H).

Preparation of [(R)-1-Hydroxymethyl-1-methyl-3-(2-phenyl-benzoxazol-5-yl)-propyl]-carbamic acid tert-butyl ester The title compound was prepared as in Example 15 using benzimidic acid ethyl ester hydrochloride. mp: 205.8/204.7° C.

EXAMPLE 17

(R)-2-Amino-2-methyl-4-[2-(4-hydroxyphenyl)-benzoxazol-5-yl]-butan-1-ol

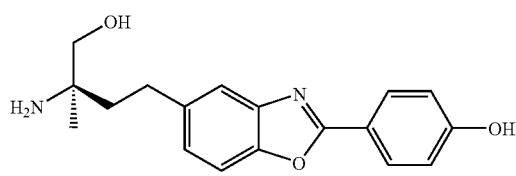

The title compound was prepared as a colorless solid as in Example 15 (Method A) using appropriate starting material. mp 229.3-231.2° C. $^1$H-NMR (DMSO-d6) δ: 8.00 (d, J=8.8 Hz; 2H), 7.62 (d, J=8.4 Hz; 1H), 7.55 (s; 1H), 7.18 (d, J=8.4 Hz; 1H), 6.97 (d, J=8.8 Hz; 2H), 5.51 (s; 1H), 3.47 (m; 2H), 2.73 (m; 2H), 1.85 (m; 2H), 1.22 (s; 3H).

Preparation of {(R)-1-Hydroxymethyl-1-methyl-3-[2-(4-hydroxyphenyl)-benzoxazol-5-yl]-}-carbamic acid tert-butyl ester The title compound was prepared as in Example 15 using 4-hydroxy-benzimidic acid ethyl ester hydrochloride. mp 136.5/133.2° C.

EXAMPLE 18

(R)-2-Amino-4-[2-(3-chloro-4-methyl-phenyl)-benzoxazol-5-yl]-2-methyl-butan-1-ol

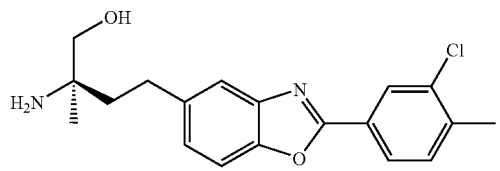

The title compound was prepared as a colorless solid as in Example 15 (Method A) using appropriate starting material. $^1$H-NMR (DMSO-d6) δ: 8.13 (s; 1H), 8.03 (d, J=8.0 Hz; 1H), 7.64 (d, J=8.4 Hz; 1H), 7.58 (m; 2H), 7.26 (d, J=8.4 Hz; 1H), 4.56 (s; 1H), 3.15 (s; 2H), 2.72 (m; 2H), 2.42 (s; 1H), 1.57 (m; 2H), 0.97 (s; 3H).

Preparation of {(R)-3-[2-(3-Chloro-4-methyl-phenyl)-benzoxazol-5-yl]-1-hydroxymethyl-1-methyl-propyl}-carbamic acid tert-butyl ester The title compound was prepared as in Example 15 using 3-Chloro-4-methyl-benzimidic acid ethyl ester hydrochloride. $^1$H-NMR (DMSO-d6) δ: 8.13 (d, J=1.7 Hz; 1H), 8.02 (dd, J=1.7, 7.9 Hz; 1H), 7.65 (d, J=8.4 Hz; 1H), 7.59 (d, J=8.2 Hz; 1H), 7.59 (d, J=8.2 Hz; 1H), 7.56 (s; 1H), 7.24 (dd, J=1.7, 8.4 Hz; 1H), 6.25 (s; 1H), 4.71 (m; 1H), 3.40 (m; 2H), 2.62 (m; 2H), 2.42 (s; 3H), 1.95 (m; 1H), 1.82 (m; 1H), 1.39 (s; 9H), 1.18 (s; 3H).

EXAMPLE 19

(R)-2-Amino-4-[2-(4-butoxy-phenyl)-benzoxazol-5-yl]-2-methyl-butan-1-ol

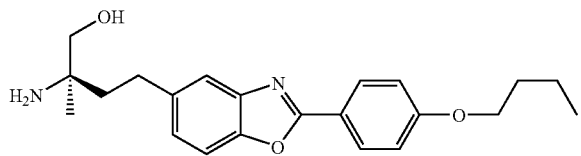

The title compound was prepared as a colorless solid as In Example 15 (Method A) using appropriate starting material. ¹H-NMR (DMSO-d6) δ: 8.09 (d, J=8.8 Hz; 2H), 7.60 (d, J=8.3 Hz; 1H), 7.52 (s; 1H), 7.18 (d, J=8.3 Hz; 1H), 7.12 (d, J=8.8 Hz; 2H), 4.56 (s; 1H), 4.07 (t; J=6.5 Hz; 2H), 3.15 (s; 2H), 2.70 (m; 2H), 1.72 (m; 2H), 1.56 (m; 2H), 1.42 (m; 2H), 0.95 (s; 3H), 0.92 (t, J=6.5 Hz; 3H).

Preparation of {(R)-3-[2-(4-Butoxy-phenyl)-benzoxazol-5-yl]-1-hydroxymethyl-1-methyl-propyl}-carbamic acid tert-butyl ester The title compound was prepared as in Example 15 using 4-Butoxy-benzimidic acid ethyl ester hydrochloride. mp 152.1/152.5° C.

EXAMPLE 20

(R)-2-Amino-4-[((E)-2-but-2-enyl)-benzoxazol-5-yl]-2-methyl-butan-1-ol

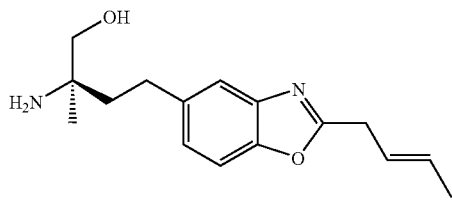

The title compound was prepared as a colorless solid as in Example 15 (Method A) using appropriate starting material. ¹H-NMR (DMSO-d6) δ: 7.51 (d, J=8.3 Hz; 1H), 7.43 (s; 1H), 7.15 (d, J=8.3 Hz; 1H), 5.66 (m; 2H), 4.57 (s; 1H), 3.63 (m; 2H), 3.16 (s; 2H), 2.68 (m; 2H), 1.68 (s; 3H), 1.54 (m; 2H), 0.96 (s; 3H).

Preparation of {(R)-3-[((E)-2-But-2-enyl)-benzoxazol-5-yl]-1-hydroxymethyl-1-methyl-propyl}-carbamic acid tert-butyl ester The title compound was prepared as in Example 15 using (E)-Pent-3-benzimidic acid ethyl ester hydrochloride. ¹H-NMR (DMSO-d6) δ: 7.52 (d, J=8.3 Hz; 1H), 7.42 (s; 1H), 7.14 (d, J=8.3 Hz; 1H), 6.23 (s; 1H), 5.16 (m; 2H), 4.69 (s; 1H), 3.62 (m; 2H), 3.38 (m; 2H), 2.58 (m; 2H), 1.92/1.78 (m; 2H), 1.66 (s; 3H), 1.66 (m; 2H), 1.38 (s; 9H), 1.15 (s; 3H).

EXAMPLE 21

(R)-2-Amino-2-methyl-4-(2-pent-4-ynyl-benzoxazol-5-yl)-butan-1-ol

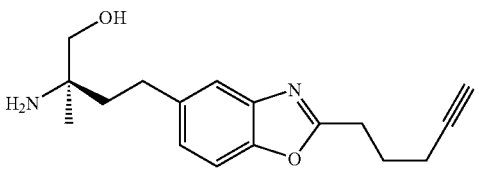

The title compound was prepared as a colorless solid as in Example 15 (Method A) using appropriate starting material. ¹H-NMR (DMSO-d6) δ: 7.52 (d, J=8.3 Hz; 1H), 7.45 (s; 1H), 7.16 (d, J=8.3 Hz; 1H), 4.54 (s; 1H), 3.14 (s; 2H), 2.98 (t, J=7.3 Hz; 2H), 2.81 (s; 1H), 2.67 (m; 2H), 2.30 (m; 2H), 1.95 (m; 2H), 1.53 (m; 2H), 0.95 (s; 3H).

Preparation of [(R)-1-Hydroxymethyl-1-methyl-3-(2-pent-4-ynyl-benzoxazol-5-yl)-propyl]-carbamic acid tert-butyl ester The title compound was prepared as in Example 15 using hex-5-ynimidic acid ethyl ester hydrochloride. ¹H-NMR (DMSO-d6) δ: 7.52 (d, J=8.3 Hz; 1H), 7.43 (s; 1H), 7.14 (d, J=8.3 Hz; 1H), 6.23 (s; 1H), 4.69 (s; 1H), 3.38 (s; 2H), 2.98 (t, J=7.3 Hz; 2H), 2.80 (s; 1H), 2.58 (m; 2H), 2.30 (m; 2H), 1.95 (m; 2H), 1.92/1.78 (m; 2H), 1.37 (s; 9H), 1.16 (s; 3H).

EXAMPLE 22

(R)-2-Amino-4-(2-cyclopropylmethyl-benzoxazol-5-yl)-2-methyl-butan-1-ol

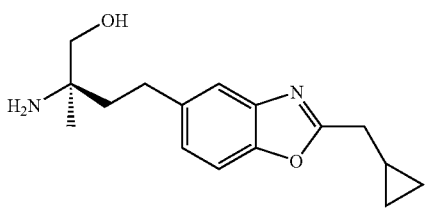

The title compound was prepared as a colorless solid as in Example 15 (Method A) using appropriate starting material. ¹H-NMR (DMSO-d6) δ: 7.52 (d, J=8.3 Hz; 1H), 7.45 (s; 1H), 7.15 (d, J=8.3 Hz; 1H), 4.56 (s; 1H), 3.14 (s; 2H), 2.82 (d, J=7.0 Hz; 2H), 2.67 (m; 2H), 1.54 (m; 2H), 1.14 (m; 1H); 0.95 (s; 3H), 0.54 (m; 2H), 0.27 (m; 2H).

Preparation of [(R)-3-(2-Cyclopropylmethyl-benzoxazol-5-yl)-1-hydroxymethyl-1-methyl-propyl]-carbamic acid tert-butyl ester The title compound was prepared as in Example 15 using 2-cyclopropyl-acetimidic acid ethyl ester hydrochloride. ¹H-NMR (DMSO-d6) δ: 7.52 (d, J=8.3 Hz; 1H), 7.43 (s; 1H), 7.13 (d, J=8.3 Hz; 1H), 6.23 (s; 1H), 4.70 (s; 1H), 3.38 (s; 2H), 2.82 (d, J=7.0 Hz; 2H), 2.58 (m; 2H), 1.93/1.80 (m; 2H), 1.38 (s; 9H), 1.16 (m; 4H); 0.52 (s; 3H), 0.27 (m; 2H).

EXAMPLE 23

((R)-2-Amino-2-methyl-4-[2-(4-trifluoromethyl-phenyl)-benzooxazol-5-yl]-butan-1-ol

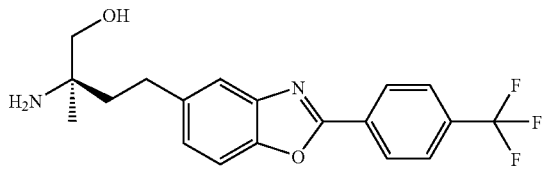

The title compound was prepared as a colorless solid as in Example 15 (Method A) using appropriate starting material. ¹H-NMR (DMSO-d6) δ: 8.37 (d, J=8.2 Hz; 2H), 7.96 (d, J=8.2 Hz; 2H), 7.69 (d, J=8.3 Hz; 1H), 7.64 (s; 3H), 7.30 (d, J=8.3 Hz; 1H), 4.58 (s; 1H), 3.16 (s; 2H), 2.72 (m; 2H), 1.57 (m; 2H); 0.96 (s; 3H).

Preparation of {(R)-1-Hydroxymethyl-1-methyl-3-[2-(trifluormethylphenyl)-benzoxazol-5-yl]-}-carbamic acid tert-butyl ester The title compound was prepared as in Example 15 using 4-trifluoromethyl benzimidic acid ethyl ester hydrochloride. ¹H-NMR (DMSO-d6) δ: 8.37 (d, J=8.2 Hz; 2H), 7.96 (d, J=8.2 Hz; 2H), 7.71 (d, J=8.3 Hz; 1H), 7.62 (s; 3H), 7.29 (d, J=8.3 Hz; 1H), 6.26 (s; 1H), 4.72 (s; 1H), 3.40 (s; 2H), 2.63 (m; 2H), 1.95/1.83 (m; 2H); 1.39 (s; 9H), 1.18 (s; 3H).

EXAMPLE 24

(R)-2-Amino-4-(2-biphenyl-4-yl-benzoxazol-5-yl)-2-methyl-butan-1-ol

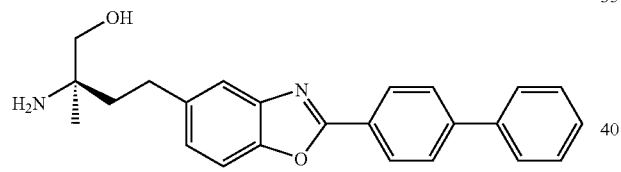

The title compound was prepared as a colorless solid as in Example 15 (Method A) using appropriate starting material. ¹H-NMR (DMSO-d6) δ: 8.23 (d, J=8.2 Hz; 2H), 7.83 (d, J=8.2 Hz; 2H), 7.71 (d, J=7.4 Hz; 2H), 7.58 (d, J=8.0 Hz; 1H), 7.55 (s; 1H), 7.46 (m; 1H), 7.38 (m; 1H), 7.22 (d; J=8.4 Hz; 1H), 3.22 (m; 2H), 2.72 (m; 2H), 1.64 (m; 2H), 1.02 (s; 3H).

Preparation of [(R)-3-(2-Biphenyl-4-yl-benzoxazol-5-yl)-1-hydroxymethyl-1-methyl-propyl]-carbamic acid tert-butyl ester The title compound was prepared as in Example 15 using biphenyl-4-carboximidic acid ethylester hydrochloride. ¹H-NMR (DMSO-d6) δ: 8.25 (d, J=8.3 Hz; 2H), 7.92 (d, J=8.3 Hz; 2H), 7.77 (d, J=7.4 Hz; 2H), 7.68 (d, J=8.0 Hz; 1H), 7.58 (s; 1H), 7.51 (m; 1H), 7.43 (m; 1H), 7.23 (d; J=8.4 Hz; 1H), 6.25 (s; 1H), 4.72 (s; 1H), 3.40 (m; 2H), 2.64 (m; 2H), 1.96/1.83 (m; 2H), 1.89 (s; 9H), 1.18 (s; 3H).

EXAMPLE 25

(R)-2-Amino-4-(2-benzo[1,3]dioxol-5-yl-benzoxazol-5-yl)-2-methyl-butan-1-ol

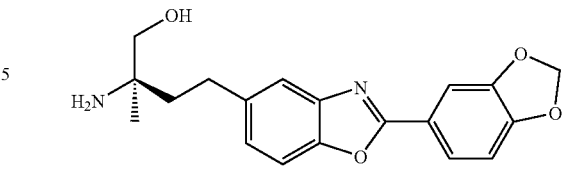

The title compound was prepared as a colorless solid as in Example 15 (Method A) using appropriate starting material. ¹H-NMR (DMSO-d8) δ: 7.73 (dd, J=8.2, 1.7 Hz; 1H), 7.60 (s; 1H), 7.59 (d, J=8.3 Hz; 1H), 7.54 (s; 1H), 7.20 (d, J=8.3 Hz; 1H), 7.12 (d, J=8.2 Hz; 1H), 6.15 (s; 2H), 4.55 (s; 1H), 3.15 (s; 2H), 2.70 (m; 2H), 1.57 (m; 2H), 0.95 (s; 3H).

Preparation of [(R)-3-(2-Benzo[1,3]dioxol-5-yl-benzoxazol-5-yl)-1-hydroxymethyl-1-methyl-propyl]-carbamic acid tert-butyl ester The title compound was prepared as in Example 15 using 2-benzo[1,3]dioxol-5-carboximidic acid ethylester hydrochloride. ¹H-NMR (DMSO-d6) δ: 7.73 (dd, J=8.2, 1.7 Hz; 1H), 7.61 (s; 1H), 7.59 (d, J=8.3 Hz; 1H), 7.50 (s; 1H), 7.18 (d, J=8.3 Hz; 1H), 7.12 (d, J=8.2 Hz; 1H), 6.24 (s; 1H), 6.15 (s; 2H), 4.71 (s; 1H), 3.39 (m; 2H), 2.62 (m; 2H), 1.95/1.81 (2m; 2H), 1.40 (s; 9H), 1.18 (s; 3H).

EXAMPLE 26

(R)-2-Amino-4-[2-(3-ethoxy-phenyl)-benzoxazol-5-yl]-2-methyl-butan-1-ol

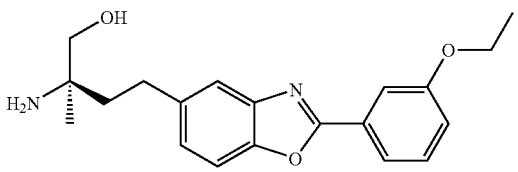

The title compound was prepared as a colorless solid as in Example 15 (Method A) using appropriate starting material. ¹H-NMR (DMSO-d6) δ: 7.74 (d, J 7.8 Hz; 1H), 7.64 (d, J=8.3 Hz; 1H), 7.63/7.57 (2s; 2H), 7.49 (t, J=8.0 Hz; 1H), 7.23 (d, J=8.3 Hz; 1H), 7.16 (m; 1H), 4.56 (s; 1H), 4.13 (q, J=7.0 Hz; 2H), 3.16 (s; 2H), 2.71 (m; 2H), 1.57 (m; 2H), 1.36 (t, J=7.0 Hz; 3H), 0.96 (s; 3H).

Preparation of {(R)-3-[2-(3-Ethoxy-phenyl)-benzoxazol-5-yl]-1-hydroxymethyl-1-methyl-propyl}-carbamic acid tert-butyl ester The title compound was prepared as in Example 15 using 3-ethoxy-benzimidic acid ethyl ester hydrochloride. ¹H-NMR (DMSO-d6) δ: 7.74 (d, J 7.8 Hz; 1H), 7.65 (d, J=8.3 Hz; 1H), 7.64/7.55 (2s; 2H), 7.49 (t, J=8.0 Hz; 1H), 7.23 (d, J=8.3 Hz; 1H), 7.16 (m; 1H), 6.24 (s; 1H), 4.72 (m; 1H), 4.13 (q, J=7.0 Hz; 2H), 3.40 (m; 2H), 2.63 (m; 2H), 1.96/1.82 (m; 2H), 1.40 (s; 9H), 1.36 (t, J=7.0 Hz; 3H), 1.18 (s; 3H).

EXAMPLE 27

(R)-2-Amino-2-methyl-4-[2-(4-phenoxy-phenyl)benzoxazol-5-yl]-butan-1-ol

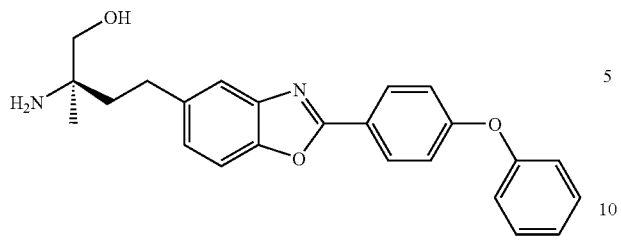

The title compound was prepared as a colorless solid as in Example 15 (Method A) using appropriate starting material. $^1$H-NMR (DMSO-$d_6$) δ: 8.16 (d, J=8.6 Hz; 2H), 7.62 (d, J=8.3 Hz; 1H), 7.55 (s; 1H), 7.46 (m; 2H), 7.23 (m; 2H), 7.14 (m; 4H), 4.57 (s; 1H), 3.15 (s; 2H), 2.71 (m; 2H), 1.57 (m; 2H), 0.96 (s; 3H).

Preparation of {(R)-1-Hydroxymethyl-1-methyl-3-[2-(4-phenoxy-phenyl)-benzoxazol-5-yl]-propyl}-carbamic acid tert-butyl ester The title compound was prepared as in Example 15 using 4-phenoxy-benzimidic acid ethyl ester hydrochloride. $^1$H-NMR (DMSO-$d_6$) δ: 8.17 (d, J=8.6 Hz; 2H), 7.63 (d, J=8.3 Hz; 1H), 7.535 (s; 1H), 7.46 (m; 2H), 7.25 (m; 1H), 7.20 (m; 1H), 7.14 (m; 4H), 6.24 (s; 1H), 4.71 (s; 1H), 3.39 (m; 2H), 2.62 (m; 2H), 1.95/1.82 (2m; 2H), 1.39 (s; 9H), 1.17 (s; 3H).

EXAMPLE 28

(R)-2-Amino-4-[2-(3,5-bis-trifluoromethyl-phenyl)-benzoxazol-5-yl]-2-methyl-butan-1-ol

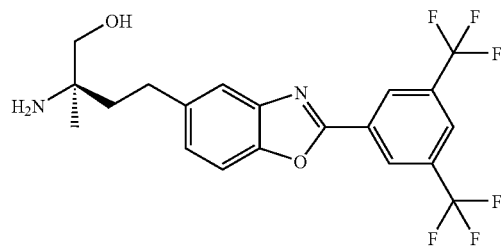

The title compound was prepared as a colorless solid as in Example 15 (Method A) using appropriate starting material. $^1$H-NMR (DMSO-$d_6$) δ: 8.65 (s; 2H), 8.40 (s; 1H), 7.72 (d; J=8.3 Hz; 1H), 7.64 (s; 1H), 7.33 (s, J=8.3 Hz; 1H), 4.58 (s; 1H), 3.18 (s; 2H), 2.73 (m; 2H), 1.58 (m; 2H), 0.95 (s; 3H).

Preparation of {(R)-3-[2-(3,5-Bis-trifluoromethyl-phenyl)-benzoxazol-5-yl]-1-hydroxymethyl-1-methyl-propyl}-carbamic acid tert-butyl ester The title compound was prepared as in Example 15 using 3,5-Bis-trifluoromethyl-benzimidic acid ethyl ester hydrochloride. $^1$H-NMR (DMSO-d6) δ: 8.68 (s; 2H), 8.40 (s; 1H), 7.73 (d; J=8.3 Hz; 1H), 7.64 (s; 1H), 7.32 (s, J=8.3 Hz; 1H), 6.27 (s; 1H), 4.72 (s; 1H), 3.40 (m; 2H), 2.64 (m; 2H), 1.96/1.83 (2m; 2H), 1.40 (s; 9H), 1.18 (s; 3H).

EXAMPLE 29

(R)-2-Amino-4-(2-furan-2-yl-benzoxazol-5-yl)-2-methyl-butan-1-ol

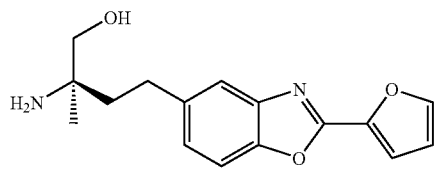

The title compound was prepared as a colorless solid as in Example 15 (Method A) using appropriate starting material. $^1$H-NMR (DMSO-$d_6$) δ: 8.59 (s; 1H), 7.92 (s; 1H), 7.58 (d, J=8.3 Hz; 1H), 7.51 (s; 1H), 7.31 (d, J=8.3 Hz; 1H), 7.05 (s; 1H), 4.58 (s; 1H), 3.16 (s; 2H), 2.70 (m; 2H), 1.58 (m; 2H), 0.95 (s; 3H).

Preparation of [(R)-3-(2-Furan-2-yl-benzoxazol-5-yl)-1-hydroxymethyl-1-methyl-propyl]-carbamic acid tert-butyl ester The title compound was prepared as in. Example 15 using furan-2-carboximidic acid ethyl ester hydrochloride. $^1$H-NMR (DMSO-$d_6$) δ: 8.60 (s; 1H), 7.92 (s; 1H), 7.60 (d, J=8.3 Hz; 1H), 7.50 (s; 1H), 7.20 (d, J=8.3 Hz; 1H), 7.05 (s; 1H), 6.23 (s; 1H), 4.70 (s; 1H), 3.40 (s; 2H), 2.61 (m; 2H), 1.94/1.82 (2m; 2H), 1.40 (s; 9H), 1.18 (s; 3H).

EXAMPLE 30

(R)-2-Amino-4-{2-[(E)-2-(3,4-dimethoxy-phenyl)-vinyl]-benzooxazol-5-yl}2-methyl-butan-1-ol

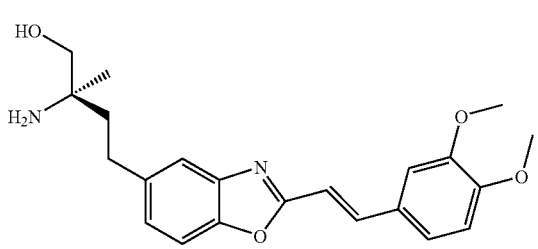

The title compound was prepared as a colorless solid as in Example 15 (Method A) using appropriate starting material. $^1$H-NMR (DMSO-$d_6$) δ: 7.70 (d; 1H), 7.54 (d; 1H), 7.49 (d; 1H), 7.44 (d; 1H), 7.29 (dd; 1H), 7.21 (d; 1H), 7.19 (d; 1H), 7.00 (d; 1H), 3.83 (s; 3H), 3.80 (s; 3H), 3.15 (bs; 2H), 2.69 (m; 2H), 1.56 (m; 2H), 1.40 (bs; 2H), 0.95 (s; 3H).

Preparation of ((R)-3-{2-[(E)-2-(3,4-Dimethoxy-phenyl)-vinyl]-benzooxazol-5-yl}-1-hydroxy-methyl-1-methyl-propyl)-carbamic acid tert-butyl ester The title compound was prepared as in Example 15 using (E)-3-(3,4-Dimethoxy-phenyl)-acrylimidic acid ethyl ester hydrochloride. Characteristic $^1$H-NMR signals (CDCl3) δ: 3.94/3.96 (2s; 6H), 1.44 (s; 9H), 1.25 (s; 3H).

EXAMPLE 31

(R)-2-Amino-4-[2-(2,2-difluoro-benzo[1,3]dioxol-5-yl)-benzooxazol-5-yl]-2-methyl-butan-1-ol

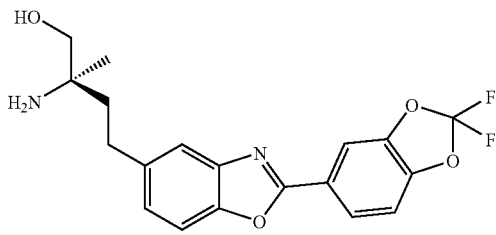

The title compound was prepared as a colorless solid as in Example 15 (Method A) using appropriate starting material. $^1$H-NMR (DMSO-d$_6$) δ: 8.14 (s; 1H), 8.04 (dd; 1H), 7.64 (t; 2H); 7.59 (s; 1H), 7.26 (d; 1H), 4.72 (bs; 1H), 3.22 (m; 2H), 2.73 (m; 2H), 1.62 (m; 2H), 1.00 (s; 3H).

Preparation of {(R)-3-[2-(2,2-Difluoro-benzo[1,3]dioxol-5-yl)-benzooxazol-5-yl]-1-hydroxy-methyl-1-methyl-propyl}-carbamic acid tert-butyl ester The title compound was prepared as in Example 15 using 2,2-Difluoro-benzo[1,3]dioxole-5-carboximidic acid ethyl ester hydrochloride. Characteristic $^1$H-NMR signals (CDCl3) δ: 8.15 (d; 1H), 8.06 (dd, 1H), 7.65/7.63 (2d; 2H), 7.56 (d; 1H), 7.24 (dd; 1H), 1.40 (s; 9H), 1.18 (s; 3H).

EXAMPLE 32

(R)-2-Amino-2-methyl-4-[2-(3-phenoxy-phenyl)-benzooxazol-5-yl]-butan-1-ol

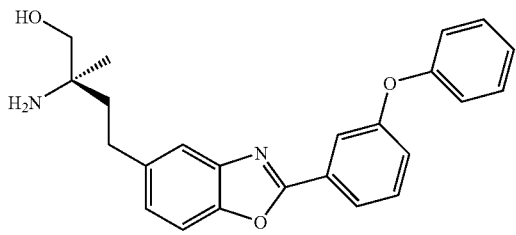

The title compound was prepared as a colorless solid as in Example 15 (Method A) using appropriate starting material. $^1$H-NMR (DMSO-d$_6$) δ: 7.90 (d; 1H), 7.68-7.52 (m; 4H), 7.45 (m; 2H), 7.25 (m; 3H), 7.12 (d; 2H), 4.63 (bs; 1H), 3.18 (s; 2H), 2.70 (m; 2H), 1.57 (m; 2H), 0.97 (s; 3H).

Preparation of {(R)-1-Hydroxymethyl-1-methyl-3-[2-(3-phenoxy-phenyl)-benzooxazol-5-yl]-propyl}-carbamic acid tert-butyl ester The title compound was prepared as in Example 15 using 3-phenoxy-benzimidic acid ethyl ester hydrochloride. Characteristic $^1$H-NMR signals (CDCl3) δ: 3.23/3.17 (AB-system; 2H), 1.44 (s; 9H), 1.25 (s; 3H).

EXAMPLE 33

(R)-2-Amino-4-[2-(4-cyclopentyloxy-3-methoxy-phenyl)-benzooxazol-5-yl]-2-methyl-butan-1-ol

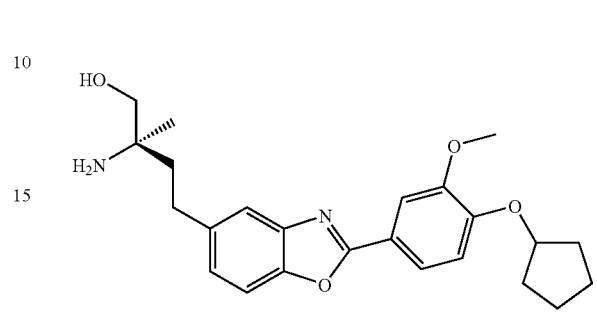

The title compound was prepared as a colorless solid as in Example 15 (Method A) using appropriate starting material. $^1$H-NMR (DMSO-d$_6$) δ: 7.73 (dd; 1H), 7.62 (d; 1H), 7.60 (d; 1H), 7.53 (s; 1H), 7.19 (d; 1H), 7.14 (d; 1H), 4.90 (bs; 1H), 4.60 (bs; 1H), 3.83 (s; 3H), 3.18 (s; 2H), 3.70 (m; 2H), 1.92 (m; 2H), 1.74 (m; 2H), 1.60 (m; 2H), 0.96 (s; 3H).

Preparation of {(R)-3-[2-(4-Cyclopentyloxy-3-methoxy-phenyl)-benzooxazol-5-yl]-1-hydroxy-methyl-1-methyl-propyl}-carbamic acid tert-butyl ester The title compound was prepared as in Example 15 using 4-cyclopentyloxy-3-methoxy-benzimidic acid ethyl ester hydrochloride. Characteristic $^1$H-NMR signals (DMSO-d6) δ: 3.83 (s; 3H), 1.39 (s; 9H), 1.18 (s; 3H).

EXAMPLE 34

(R)-2-Amino-4-[2-(2,3-dimethoxy-phenyl)-benzooxazol-5-yl]-2-methyl-butan-1-ol

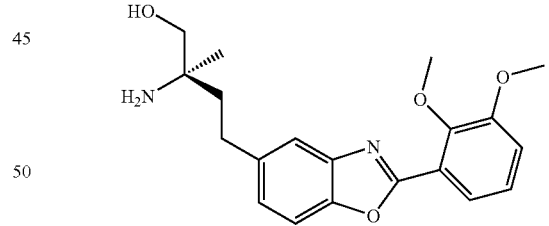

The title compound was prepared as a colorless solid as in Example 15 (Method A) using appropriate starting material. $^1$H-NMR (DMSO-d$_6$) δ: 7.60 (bs; 3H), 7.28 (bs; 3H), 3.90 (bs; 6H), 3.20 (bs; 2H), 2.75 (bs; 2H), 1.60 (bs; 1H), 0.98 (bs; 3H).

Preparation of {(R)-3-[2-(2,3-Dimethoxy-phenyl)-benzooxazol-5-yl]-1-hydroxymethyl-1-methyl-propyl}-carbamic acid tert-butyl ester The title compound was prepared as in Example 15 using 2,3-Dimethoxy-benzimidic acid ethyl ester hydrochloride. Characteristic $^1$H-NMR signals (DMSO-d$_6$) δ: 3.85/3.87 (2s; 6H), 1.39 (s; 9H), 1.19 (s; 3H).

EXAMPLE 35

(R)-2-Amino-4-[2-(2,5-dimethoxy-phenyl)-benzooxazol-5-yl]-2-methyl-butan-1-ol

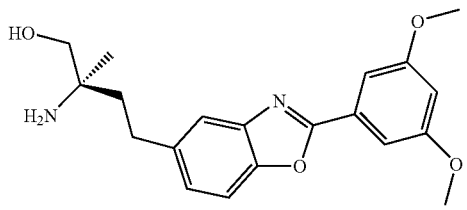

The title compound was prepared as a colorless solid as in Example 15 (Method A) using appropriate starting material.
¹H-NMR (DMSO-d₆) δ: 7.64 (d; 1H), 7.57 (s; 1H), 7.27 (d; 2H), 7.24 (dd; 1H), 6.63 (t; 1H), 4.60 (bs; 1H), 3.34 (s; 6H), 3.17 (s; 2H), 2.70 (m; 2H), 1.58 (m; 2H), 0.95 (s; 3H).

Preparation of {(R)-3-[2-(2,5-Dimethoxy-phenyl)-benzooxazol-5-yl]-1-hydroxymethyl-1-methyl-propyl}-carbamic acid tert-butyl ester The title compound was prepared as in Example 15 using 2,5-Dimethoxy-benzimidic acid ethyl ester hydrochloride. Characteristic ¹H-NMR signals (CDCl3) δ: 3.90 (s; 6H), 1.44 (s; 9H), 1.26 (s; 3H).

EXAMPLE 36

(R)-2-Amino-2-methyl-4-[2-(4-phenyl-5-trifluoromethyl-thiophen-2-yl)-benzo-oxazol-5-yl]-butan-1-ol

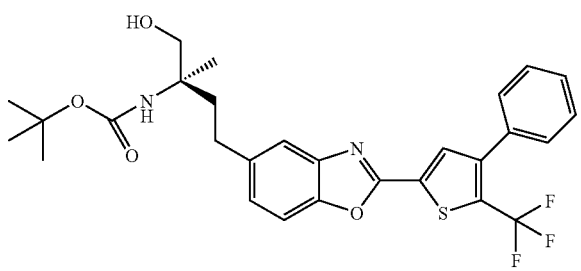

The title compound was prepared as a colorless solid as in Example 15 (Method A) using appropriate starting material.
¹H-NMR (DMSO-d₈) δ: 8.03 (s; 1H), 7.67 (d; 1H), 7.61 (s; 1H), 7.56-7.45 (m; 5H), 7.30 (dd; 1H), 4.59 (bs; 1H), 3.17 (s; 2H), 2.73 (m; 2H), 1.58 (m; 2H), 0.97 (s; 3H).

EXAMPLE 37

(R)-2-Amino-2-methyl-4-(2-phenyl-benzofuran-5-yl)-butan-1-ol

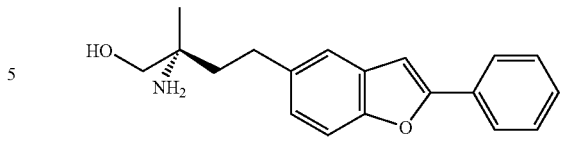

The title compound was synthesized by following the procedure described in Synthesis (2003), (11), 1667-1670.
¹H-NMR (DMSO-d₆): 7.88 (d, J=7.39 Hz, 2H), 7.48 (t, J=6.12 Hz, 2H), 7.42 (s, 1H), 7.40 (m, 2H), 7.34 (s, 1H), 7.12 (d, J=7.68 Hz, 1H), 4.57 (br, s, 1H, OH), 3.17 (s, 2H), 2.68 (m, J=8.65 Hz, 2H), 1.58 (t, J=8.8 Hz, 2H), 1.45 (br, s, 2H; —NH₂), 0.98 (s, 3H). MS (ESI⁺): 296.3 [M+H]⁺

Preparation of 5-(2-iodo-ethyl)-2-phenyl-benzofuran 2-(2-Phenyl-benzofuran-5-yl)ethanol (11.18 g; 46.9 mmol) was dissolved in DCM (170 ml) and N-iodinesuccinimide (NIS; 11.31 g; 50.27 mmol) and triphenylphosphine (15.39 g; 52.67 mmol) was added under stirring. After keeping the reaction mixture at RT over night the reaction was extracted two times with 6% aqueous NaHCO₃ solution and the organic layer was dried over Na₂SO₄. After filtering and removal of the solvent pure title compound was obtained after crystallization from methanol/DCM/cyclo-hexane. The mother liquor was collected and purified on silica gel (cyclohexane/ethylacetate 95/5 as mobile phase).

Preparation of 2-(2-Phenyl-benzofuran-5-yl)-ethanol

2-Phenyl-benzofuran-5-yl)-acetic acid ethyl ester (Ota et al; Journal of the Chemical Society, Perkin Transactions 1: Organic and Bio-Organic Chemistry (1972-1999) (1988), (11), 3029-35; 13.14 g; 46.87 mmol) was dissolved in dry THF. After addition of LiAlH₄ (2.85 g; 74.99 mmol) the reaction was kept at 80° C. for 1 hour. After cooling to RT the reaction was slowly poured into saturated aqueous Na₂SO₄ solution (150 ml) and filtered over Hyflo. The solvent was removed under reduced pressure and the residue was dissolved in AcOEt and extracted 2 times with water. The organic layer was dried over Na₂SO₄. The pure title compound was obtained after removal of the solvent.

EXAMPLE 38

(R)-2-Amino-4-[2-(4-fluoro-phenyl)benzofuran-5-yl]-2-methyl-butan-1-ol

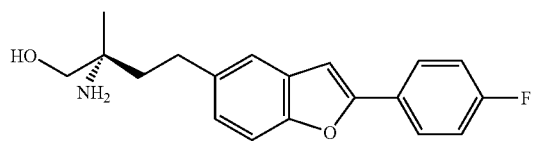

The title compound was synthesized by following the procedure described for example 30 and using 4-fluoro-phenacylchloride as starting material for the synthesis of [2-(4-fluoro-phenyl)-benzofuran-5-yl]-acetic acid ethyl ester.
¹H-NMR (DMSO-d₆) δ: 7.94 (d, J=8.78 Hz, 1H), 7.92 (d, J=8.72 Hz, 1H), 7.48 (d, J=8.33 Hz, 1H), 7.42 (s, 1H), 7.35-7.29 (m, 3H), 7.12 (d, J=8.34 Hz, 1H), 4.58 (br, s, 1H; —OH), 3.17 (s, 2H), 2.68 (m, J=8.65 Hz, 2H), 1.58 (t, J=8.33 Hz, 2H), 1.23 (br, s, 2H; —NH$_2$), 0.98 (s, 3H). MS (ESI$^+$): [M+H]$^+$

EXAMPLE 39

2-Amino-2-[2-(2-phenyl-benzofuran-5-yl)-ethyl]-propane-1,3-diol

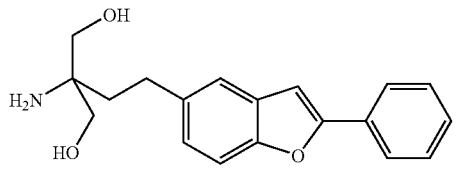

The title compound was prepared by following the procedure in Journal of Medicinal Chemistry (2000 Jul. 27), 43(15), 2946-61) using 5-(2-iodo-ethyl)-2-phenyl-benzofuran as alkylating reagent in scheme 6 (step g). $^1$H-NMR (DMSO-d$_6$) δ: 7.88 (d, J=7.58 Hz, 2H), 7.55-7.30 (m, 6H), 7.12 (d, J=8.34 Hz, 1H), 4.43 (br, s, 2H; —OH); 3.26 (m, 4H), 2.68 (m, 2H), 1.56 (m, 2H), 1.28 (s, 2H; —NH$_2$). MS (ESI$^+$): 312.4 [M+H]$^+$

EXAMPLE 40

2-Amino-2-[2-(3-ethyl-1-methyl-1H-indazol-5-yl)-ethyl]-propane-1,3-diol

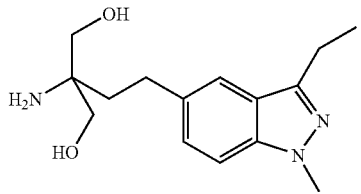

The title compound was synthesized by following the procedure described in Tetrahedron Letters (2002), 43(45), 8095-8097; using 5-(2-iodo-ethyl)-2-phenyl-benzofuran as alkylating reagent in the Schöllkopf reaction. $^1$H-NMR (DMSO-d6): 7.57 (d, J=8.21 Hz, 1H), 7.27 (s, 1H), 6.92 (d, J=8.27 Hz, 1H), 4.45 (br, s, 2H; —OH), 3.90 (s, 3H; —NCH3), 3.25 (q, J=8.08 Hz, 4H), 2.85 (q, J=7.58 Hz, 2H), 2.72 (m, 2H). 1.57 (m, 2H). 1.28 (t, J=7.52 Hz, 3H). MS (ESI+): 312.4 [M+H]+

EXAMPLE 41

2-Amino-2-[2-(3-heptyl-1-methyl-1H-indazol-5-yl)-ethyl]-propane-1,3-diol

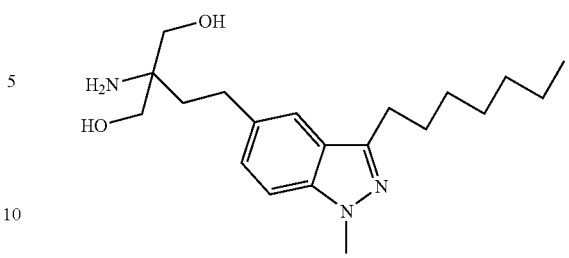

The title compound was synthesized by following the procedure described in Tetrahedron Letters (2002), 43(45), 8095-8097; using 5-(2-iodo-hepthyl)-2-phenyl-benzofuran (prepared similar to 5-(2-iodo-ethyl)-2-phenyl-benzofuran) as alkylating reagent in the Schöllkopf reaction. $^1$H-NMR (DMSO-d$_6$) δ: 7.55 (d, J=8.22 Hz, 1H), 7.27 (s, 1H), 6.91 (d, J=8.27 Hz, 1H), 4.99 (br, s, 3H; —NH$_2$; —OH), 3.90 (s, 3H; —NCH3), 3.25 (m, 4H), 2.82 (t, J=7.51 Hz, 2H), 2.71 (m, 2H), 1.69 (m, 2H), 1.61 (m, 2H), 1.35-1.15 (m, 8H), 0.85 (t, J=6.37 Hz, 3H). MS (ESI+): 348.5 [M+H]+

EXAMPLE 42

Phosphoric acid mono-[(R)-2-amino-2-methyl-4-(2-pentyl-benzoxazol-5-yl)-butyl]ester

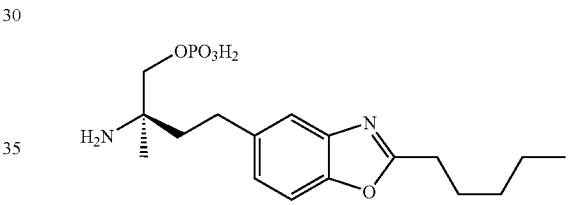

A solution of [(R)-1-Methyl-3-(2-pentyl-benzoxazol-5-yl)-1-phosphonooxymethyl-propyl]-carbamic acid tert-butyl ester ammonium salt (18 mg, 0.0369 mmol) in diethyl ether (2 ml) was treated with 2M HCl in diethyl ether and stirred for 2 hours at RT. The reaction was quenched by the addition of a solution of 28% aqueous ammonium hydroxide (2 ml), methanol (2 ml) and DCM (1 ml). After evaporation of the solvents in vacuum the residue was purified using preparative reversed phase chromatography (X-Terra, C-18, eluent: gradient of 10 mM NH$_4$HCO$_3$ in water/acetonitrile. The title compound was obtained as an amorphous solid. MS(MH−) 269.3.

Preparation of [(R)-1-Methyl-3-(2-pentyl-benzoxazol-5-yl)-1-phosphonooxymethyl-propyl]-carbamic acid tert-butyl ester ammonium salt Under an atmosphere of argon 10% Pd on charcoal (50 mg) was added to a solution of [(R-1-Methyl-1-(3-oxo-1,5-dihydro-benzo[e][1,3,2]dioxaphosphepin-3-yloxymethyl)-3-(2-pentyl-benzoxazol-5-yl)propyl]-carbamic acid tert-butyl ester (168.5 mg, 0.2942 mmol) in ethanol (20 ml). Argon was replaced by hydrogen and the reaction was allowed to proceed for 8 hours. 28% aqueous ammonium hydroxide was added until basic and the solvents evaporated in vacuum. The residue was purified by preparative reversed phase chromatography (X-Terra, C-18, eluent: gradient of 10 mM NH$_4$HCO$_3$ in water/acetonitrile). The title compound was obtained as an amorphous solid. MS(MH−) 469.3.

[(R)-1-Methyl-1-(3-oxo-1,5-dihydro-benzo[e][1,3,2] dioxaphosphepin-3-yloxymethyl)-3-(2-pentyl-benzoxazol-5-yl)-propyl]-carbamic acid tert-butyl ester Under an atmosphere of argon a solution of [(R)-1-Hydroxymethyl-1-methyl-3-(2-pentyl-benzoxazol-5-yl)-propyl]-carbamic acid tert-butyl ester (151 mg, 0.387 mmol) and tetrazole (85 mg, 1.21 mmol) in dry THF (3 ml) was treated with N,N-diethyl-1,5-dihydro-2,4,3-benzo-dioxaphosphepin-3-amine (185 mg, 0.77 mmol) and stirred for 1 hours at RT. After cooling the reaction mixture to 0° C., aqueous hydrogen peroxide (0.4 ml of a 30 w/w % solution) was added and the reaction was allowed to stir for one hour at RT. The reaction mixture was distributed between a 10% aqueous Na$_2$S$_2$O$_3$ solution and AcOEt. The organic layer was dried over MgSO$_4$, concentrated in vacuum and purified over silica gel (eluent (DCM/methanol 30/1). The title compound was obtained as an colorless amorphous solid. $^1$H-NMR (DMSO-d6) δ: 7.52 (d, J=8.3 Hz; 1H), 7.50-7.40 (m; 5H), 7.15 (dd, J=8.3, 1.5 Hz; 1H), 6.8 (bs; 1H), 5.32-5.26/5.16-5.04 (m; 4H), 4.17/4.06 (AB-system, J=9.5, 4.5 Hz; 2H), 2.88 (t, J=7.5 Hz; 2H), 2.71-2.58 (m; 2H), 2.14-2.08 (m; 1H), 1.81-1.68 (m; 3H), 1.38 (s; 9H); 1.28 (s; 3H), 1.38-1.28 (m; 4H), 0.85 (m; 3H).

EXAMPLE 43

Phosphoric acid mono-{(R)-2-amino-4-[2-(3-ethoxy-phenyl)-benzooxazol-5-yl]-2-methyl-butyl}ester hydrochloride

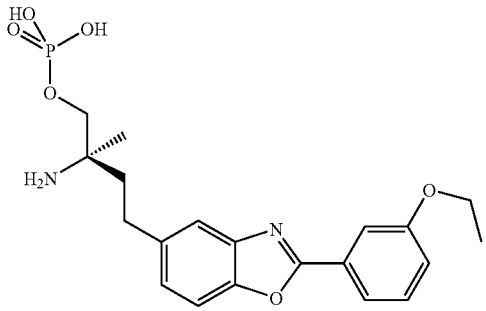

A solution of [(R)-3-(3-Amino-4-hydroxy-phenyl)-1-(di-tert-butoxy-phosphoryloxymethyl)-1-methyl-propyl]-carbamic acid tert-butyl ester (157.5 mg, 0.313 mmol) and 3-ethoxy-benzimidic acid ethyl ester hydrochloride in dry methanol (2 mL) was stirred for 20 minutes at 120° C. in a closed vial (microwave reactor). After cooling to RT the precipitate was filtered off, washed 2× with MeOH, 3× with water and 3× with diethyl ether. After drying in vacuum, the precipitate was dissolved in a mixture of diethyl ether/HCl (4 mL, 2M) and methanol (1 mL). After evaporation of the solvents the title compound was obtained as colorless crystals. $^1$H-NMR (CD3OD): δ=7.76 (d; 1H), 7.71 (s; 1H), 7.61 (bs; 2H), 7.47 (m; 1H), 7.37 (m; 1H), 7.14 (d; 1H), 4.24-4.00 (m; 4H), 2.89 (m; 2H), 2.10 (m; 2H), 1.47 (s; 6H); MS (ESI$^+$): 421.4 [M+H]$^+$

Preparation of [(R)-3-(3-Amino-4-hydroxy-phenyl)-1-(di-tert-butoxy-phosphoryloxymethyl)-1-methyl-propyl]-carbamic acid tert-butyl ester Under an atmosphere of argon, a solution of [(R)-3-(4-Benzyloxy-3-nitro-phenyl)-1-(di-tert-butoxy-phosphoryloxymethyl)-1-methyl-propyl]-carbamic acid tert-butyl ester (5.36 g, 8.6 mmol) in ethanol (250 mL) was treated with 10% palladium on charcoal (1.22 g). Argon was replaced by hydrogen and the reaction was stirred for 16 hours at RT. After filtration and removal of the solvent in vacuum, the residue was purified by silica gel column chromatography (dichloromethane/methanol 10/1) yielding the title compound as a colorless solid. $^1$H-NMR (CD$_3$OD): δ=6.61-6.57 (m; 2H), 6.41 (dd; 1H), 6.22 (s; 1H), 4.55 (s; 1H), 4.41/3.93 (2m; 2H), 2.43 (m; 1H), 2.05 (m; 1H), 1.70 (m; 1H), 1.48 (s; 18H), 1.44 (s; 9H), 1.28 (s; 3H); MS (ESI$^+$): 503.4 [M+H]$^+$

Preparation of [(R)-3-(4-Benzyloxy-3-nitro-phenyl)-1-(di-tert-butoxy-phosphoryloxymethyl)-1-methyl-propyl]-carbamic acid tert-butyl ester Under an atmosphere of argon, a solution of [(R)-3-(4-Benzyloxy-3-nitro-phenyl)-1-hydroxymethyl-1-methyl-propyl]-carbamic acid tert-butyl ester (3.71 g, 8.62 mmol) in tetrahydrofuran (71 mL) was treated with tetrazole (1.89 g, 27.0 mmol) and di-tert-butyl diethyl phosphoramidite (4.8 mL, 17.24 mmol). After stirring for 100 minutes at room temperate, hydrogen peroxide (9 mL of a 30% solution In water) was carefully added (exothermic). After stirring for additional 60 minutes at room temperature, the reaction mixture was distributed between a solution of Na$_2$S$_2$O$_3$ (10% in water) and AcOEt. The organic layer was dried over magnesium sulfate and evaporated in vacuum (colorless oil). MS (ESI$^+$): 623.4 [M+H]$^+$

Preparation of [(R)-3-(4-Benzyloxy-3-nitro-phenyl)-1-hydroxymethyl-1-methyl-propyl]-carbamic acid tert-butyl ester A solution of [(R)-3-(3-Amino-4-hydroxy-phenyl)-1-hydroxymethyl-1-methyl-propyl]-carbamic acid tert-butyl ester (3.27 g, 9.60 mmol) in dimethylformamide (64 mL) was treated with potassium carbonate (2.65 g, 19.2 mmol) and benzylbromide (1.15 mL, 9.6 mmol) and stirred for 20 hours at 80° C. After filtration, the filtrate was evaporated in vacuum, redissolved in dichloromethane and extracted with 1N aqueous HCl, saturated aqueous sodium hydrogen carbonate solution and brine. After drying the organic phase over magnesium sulfate and removal of the solvents in vacuum, the title compound crystallized from pentane to yield the title compound as pale yellow crystals. $^1$H-NMR (DMSO-d6): δ 7.70 (d; 1H), 7.55-7.29 (m; 7H), 6.27 (bs; 1H), 5.75 (s; 2H), 4.69 (t; 1H), 3.37 (m; 2H), 2.51 (m; 2H), 1.87 (m; 1H), 1.72 (m; 1H), 1.36 (s; 9H), 1.15 (s; 3H); MS (ESI$^+$): 431.3 [M+H]$^+$

EXAMPLES 44 TO 48

The examples shown in Table 3 are prepared as described in ex. 43.

TABLE 3

| Ex. | wherein R' | $^1$H-NMR (CD$_3$OD) |
|---|---|---|
| 44 | (benzo[d][1,3]dioxol-5-yl) | 7.73 (dd; 1H), 7.66 (d; 1H), 7.60 (m; 2H), 7.33 (dd; 1H), 7.05 (d; 1H), 6.12 (s; 2H), 4.17/4.04 (2 m; 2H), 2.88 (m; 2H), 2.15/2.05 (2 m; 2H), 1.49 (s; 3H) |
| 45 | (p-tolyl) | 8.25 (d; 2H), 7.57-7.68 (m; 5H), 7.37 (d; 1H), 4.17/4.06 (2 m; 2H), 2.90 (m; 2H), 2.10 (m; 2H), 1.48 (s; 3H) |
| 46 | (2-chloro-4-methylphenyl — CH$_3$, Cl substituted) | 8.10 (d; 1H), 7.95 (dd; 1H), 7.54 (m; 2H), 7.43 (d; 1H), 7.26 (dd; 1H), 4.06/3.96 (ABX-system; 2H), 2.79 (m; 2H), 2.39 (s; 3H), 2.08-1.88 (m; 2H), 1.38 (s; 3H) |
| 47 | (4-butoxyphenyl) | 8.06 (d; 2H), 7.49 (m; 2H), 7.20 /d; 1H), 7.02 (d; 2H), 4.07-3.90 (m; 2H), 4.02 (t; 2H), 2.78 (m; 2H9, 2.08-1.88 (m; 2H), 1.72 (m; 2H), 145 (m; 2H), 1.38 (s; 3H), 0.92 (t; 3H) |
| 48 | (4-phenoxyphenyl) | 8.21 (d; 2H), 7.62 (m; 2H), 7.45 (m; 2H), 7.34 (d; 1H); 7.24 (d; 1H), 7.13 (m; 4H), 4.40-4.00 (m; 2H), 2.88 (m; 2H), 2.20-2.00 (m; 2H), 1.48 (s; 3H) |

EXAMPLE 49

Phosphoric acid mono-[(R)-2-amino-2-methyl-4-(2-phenyl-benzofuran-5-yl)-butyl]ester

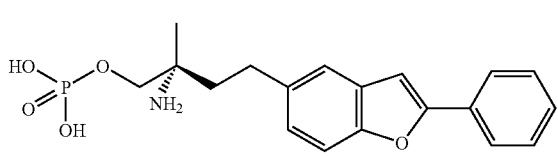

The title compound was synthesized by following the procedure described in Synthesis (2003), (11), 1667-1670. $^1$H-NMR (MeOD+DCl) δ: 7.86 (d, J=7.96, 2H), 7.50-7.30. (m, 5H), 7.19 (d, J=8.44 Hz, 1H), 7.13 (s, 1H), 4.09 (m, 2H), 2.82 (m, 2H), 2.09 (m, 2H), 1.47 (s, 3H). MS (ESI$^+$): 376.4 [M+H]$^+$

EXAMPLE 50

Phosphoric acid mono-{(R)-2-amino-4-[2-(4-fluoro-phenyl)-benzofuran-5-yl]-2-methyl-butyl}ester

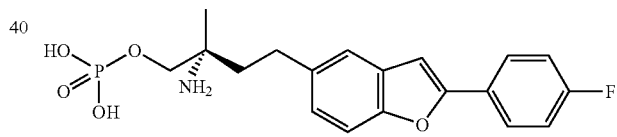

The title compound was synthesized by following the procedure described In Synthesis (2003), (11), 1667-1670. $^1$H-NMR (MeOD+DCl) δ: 7.91 (d, J=8.65, 2H), 7.90 (d, J=8.65, 2H), 7.49 (s, 1H), 7.44 (d, J=8.21, 1H), 7.20 (m, 2H), 7.09 (s, 1H), 4.09 (m, 2H), 2.82 (m, 2H), 2.08 (m, 2H), 1.46 (s, 3H). $^{31}$P-NMR (MeOD+DCl) δ: −0.45; MS (ESI$^-$): 392 [M−H]$^-$ The compounds of formula I in free form or in pharmaceutically acceptable salt form, exhibit valuable pharmacological properties, e.g. lymphocyte recirculation modulating properties, e.g. as indicated in in vitro and in vivo tests and are therefore indicated for therapy.

A. In vitro

The compounds of formula I have binding affinity to individual human S1P receptors as determined in following assays:

Sphingosine-1-phosphate (S1P) Receptor Profiling

Agonist activities of compounds are tested on the human S1P receptors EDG-1 (S1P$_1$), EDG-3 (S1P$_3$), EDG-5 (S1P$_2$), EDG-6 (S1P$_4$) and EDG-8 (S1P$_5$). Functional receptor activation is assessed by quantifying compound induced GTP [γ-$^{35}$S] binding to membrane protein prepared from transfected CHO or RH7777 cells stably expressing the appropriate human S1P receptor. The assay technology used is SPA (scintillation proximity based assay). Briefly, DMSO dissolved compounds are serially diluted and added to SPA-bead (Amersham-Pharmacia) immobilised S1P receptor expressing membrane protein (10-20 µg/well) in the presence of 50 mM Hepes, 100 mM NaCl, 10 mM MgCl$_2$, 10 µM GDP, 0.1% fat free BSA and 0.2 nM GTP [γ-$^{35}$S] (1200 Ci/mmol). After incubation in 96 well microtiterplates at RT for 120 min, unbound GTP [γ-$^{35}$S] is separated by a centrifugation step. Luminescence of SPA beads triggered by membrane bound GTP [γ-$^{35}$S] is quantified with a TOPcount plate reader (Packard). EC$_{50}$s are calculated using standard curve fitting software. In this assay, the compounds of formula I have a binding affinity to S1P$_1$ receptor <50 nM.

| Compound of Ex. | S1P$_1$ EC$_{50}$ [nM] | S1P$_3$ EC$_{50}$ [nM] | S1P$_4$ EC$_{50}$ [nM] | S1P$_5$ EC$_{50}$ [nM] |
|---|---|---|---|---|
| 12 | 0.3 Agon | 8.4 Agon | 0.4 Agon | 0.1 Agon |
| 13 | 0.06 Agon | 5.7 Agon | 1.2 Agon | 0.4 Agon |
| 14 | 2.8 Agon | 47 inverse Agon | 1.0 Agon | 0.8 Agon |
| 42 | 17 Agon | >1000 Agon | 9 Agon | 5 Agon |
| 49 | 1.6 Agon | 1180 Agon | 0.7 Agon | 0.4 Agon |

Agon = agonist

B. In vivo: Blood Lymphocyte Depletion

A compound of formula I or the vehicle is administered orally by gavage to rats. Tail blood for hematological monitoring is obtained on day −1 to give the baseline individual values, and at 2, 6, 24, 48 and 72 hours after application. In this assay, the compounds of formula I deplete peripheral blood lymphocytes when administered at a dose of 0.03 to 3 mg/kg. For example, following results are obtained: depletion of peripheral blood lymphocytes by more than 50%.

| | | |
|---|---|---|
| Example 1: | 0.02 mg/kg p.o. after 6 h, 0.3 mg/kg p.o. after 24 h, | >1 mg/kg after 48 h |
| Example 6: | 0.07 mg/kg p.o. after 6 h | |
| Example 25: | 0.06 mg/kg p.o. after 6 h | 0.3 mg/kg after 48 h |
| Example 26: | 0.03 mg/kg p.o. after 6 h | 0.2 mg/kg after 48 h |
| Example 37: | 0.40 mg/kg p.o. after 6 h | |

The compounds of formula I are, therefore, useful in the treatment and/or prevention of diseases or disorders mediated by lymphocytes interactions, e.g. in transplantation, such as acute or chronic rejection of cell, tissue or organ allo- or xenografts or delayed graft function, graft versus host disease, autoimmune diseases, e.g. rheumatoid arthritis, systemic lupus erythematosus, hashimoto's thyroldis, multiple sclerosis, myasthenia gravis, diabetes type I or II and the disorders associated therewith, vasculitis, pernicious anemia, Sjoegren syndrome, uveitis, psoriasis, Graves ophthalmopathy, alopecia areata and others, allergic diseases, e.g. allergic asthma, atopic dermatitis, allergic rhinitis/conjunctivitis, allergic contact dermatibs, inflammatory diseases optionally with underlying aberrant reactions, e.g. inflammatory bowel disease, Crohn's disease or ulcerative colitis, Intrinsic asthma, inflammatory lung injury, inflammatory liver injury, inflammatory glomerular injury, atherosclerosis, osteoarthribs, irritant contact dermatitis and further eczematous dermatitises, seborrhoeic dermatitis, cutaneous manifestations of immunologically-mediated disorders, inflammatory eye disease, keratoconjunctivitis, myocarditis or hepatitis, ischemia/reperfusion injury, e.g. myocardial infarcton, stroke, gut ischemia, renal failure or hemorrhage shock, traumatic shock, angiogenesis, Alzheimer's disease, cancer, e.g. breast cancer, T cell lymphomas or T cell leukemias, infectious diseases, e.g. toxic shock (e.g. superantigen induced), septic shock, adult respiratory distress syndrome or viral infections, e.g. AIDS, viral hepatitis, chronic bacterial Infection, or senile dementia. Examples of cell, tissue or solid organ transplants include e.g. pancreatic Islets, stem cells, bone marrow, corneal tissue, neuronal tissue, heart, lung, combined heart-lung, kidney, liver, bowel, pancreas, trachea or oesophagus. For the above uses the required dosage will of course vary depending on the mode of administration, the particular condition to be treated and the effect desired.

In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, for example, in divided doses up to four times a day or in retard form. Suitable unit dosage forms for oral administration comprise from ca. 0.1 to 50 mg active ingredient.

The compounds of formula I may be administered by any conventional route, in particular enterally, e.g. orally, e.g. in the form of tablets or capsules, or parenterally, e.g. in the form of injectable solutions or suspensions, topically, e.g. in the form of lotions, gels, ointments or creams, or in a nasal or a suppository form. Pharmaceutical compositions comprising a compound of formula I in free form or in pharmaceutically acceptable salt form In association with at least one pharmaceutical acceptable carrier or diluent may be manufactured in conventional manner by mixing with a pharmaceutically acceptable carrier or diluent.

The compounds of formula I may be administered In free form or in pharmaceutically acceptable salt form e.g. as indicated above. Such salts may be prepared in conventional manner and exhibit the same order of activity as the free compounds.

In accordance with the foregoing the present invention further provides:

1.1 A method for preventing or treating disorders or diseases mediated by lymphocytes, e.g. such as indicated above, in a subject In need of such treatment, which method comprises administering to said subject an effective amount of a compound of formula I or a pharmaceutically acceptable salt thereof;

1.2 A method for preventing or treating acute or chronic transplant rejection or T-cell mediated inflammatory or autoimmune diseases, e.g. as indicated above, in a subject in need of such treatment, which method comprises administering to said subject an effective amount of a compound of formula I or a pharmaceutically acceptable salt thereof;

2. A compound of formula I, in free form or In a pharmaceutically acceptable salt form for use as a pharmaceutical, e.g. in any of the methods as indicated under 1.1 or 1.2 above.

3. A pharmaceutical composition, e.g. for use in any of the methods as in 1.1 or 1.2 above comprising a compound of formula I in free form or pharmaceutically acceptable salt form in association with a pharmaceutically acceptable diluent or carrier therefor.

4. A compound of formula I or a pharmaceutically acceptable salt thereof for use in the preparation of a pharmaceutical composition for use in any of the method as in 1.1 or 1.2 above.

The compounds of formula I may be administered as the sole active ingredient or in conjunction with, e.g. as an adjuvant to, other drugs e.g. immunosuppressive or immunomodulating agents or other anti-inflammatory agents, e.g. for the treatment or prevention of allo- or xenograft acute or chronic rejection or inflammatory or autoimmune disorders, or a chemotherapeutic agent, e.g a malignant cell anti-proliferative agent. For example, the compounds of formula I may be used in combination with a calcineurin inhibitor, e.g. cyclosporin A, FK 506 or ISA$_{TX}$247; a mTOR inhibitor, e.g. rapamycin, 40-O-(2-hydroxyethyl)-rapamycin, CC1779, ABT578, AP23573, AP23464, AP23675, AP23841, TAFA-93, biolimus 7 or biolimus 9; an ascomycin having Immunosuppressive properties, e.g. ABT-281, ASM981, etc.; a S1P receptor agaonist e.g. FTY720 or an analogue thereof; corticosteroids; cyclophosphamide; azathioprene; methotrexate; leflunomide; mizoribine; mycophenolic acid; mycophenolate mofetil; 15-deoxyspergualine or an immunosuppressive homologue, analogue or derivative thereof; immunosuppressive monoclonal antibodies, e.g., monoclonal antibodies to leukocyte receptors, e.g., MHC, CD2, CD3, CD4, CD7, CD8, CD25, CD28, CD40. CD45, CD58, CD80, CD86 or their ligands; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4lg (for ex. designated ATCC 68629) or a mutant thereof, e.g. LEA29Y; adhesion molecule inhibitors, e.g. LFA-1 antagonists, ICAM-1 or -3 antagonists, VCAM4 antagonists or VLA4 antagonists; or a chemotherapeutic agent, e.g. paclitaxel, gemcitabine, cisplatinum, doxorubicin or 5-fluorouracil; or an anti-infectious agent.

Where the compounds of formula I are administered in conjunction with other immunosuppressive/immunomodulatory, anti-inflammatory. chemotherapeutic or anti-infectious therapy, dosages of the co-administered immunosuppressant, immunomodulatory, anti-inflammatory, chemotherapeutic or ant-infectious compound will of course vary depending on the type of co-drug employed, e.g. whether it is a steroid or a calcineurin Inhibitor, on the specific drug employed, on the condition being treated and so forth. In accordance with the foregoing the present invention provides in a yet further aspect:

5. A method as defined above comprising co-administration, e.g. concomitantly or in sequence, of a therapeutically effective non-toxic amount of a compound of formula I and at least a second drug substance, e.g. an immunosuppressant, immunomodulatory, anti-inflammatory or chemotherapeutic drug, e.g. as indicated above.
6. A pharmaceutical combination, e.g. a kit, comprising a) a first agent which is a compound of formula I as disclosed herein, in free form or in pharmaceutically acceptable salt form, and b) at least one co-agent, e.g. an immunosuppressant, immunomodulatory, anti-inflammatory, chemotherapeutic or anti-infectious agent. The kit may comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of formula I and a co-agent, are both administered to a patient simultaneously in the form of a single entity or dosage. The term "non-fixed combination" means that the active ingredients, e.g. a compound of formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

The invention claimed is:
1. A compound of formula I

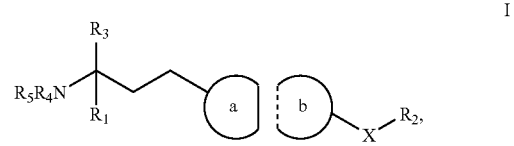

wherein
R$_1$ is C$_{1-6}$alkyl; C$_{1-6}$alkyl substituted by hydroxy, C$_{1-2}$alkoxy, or 1 to 6 fluorine atoms; C$_{2-6}$alkenyl; or C$_{2-6}$alkynyl;
X is O, CH$_2$, C=O or a direct bond;
R$_2$ is optionally substituted C$_{1-7}$alkyl, optionally substituted C$_{1-7}$alkenyl, optionally substituted C$_{1-7}$alkinyl, optionally substituted C$_{3-6}$cycloalkyl, optionally substituted phenyl, or optionally substituted heteroaryl,
  where the substituted C$_{1-7}$alkyl, C$_{1-7}$alkinyl or C$_{3-6}$cycloalkyl has 1 to 5 substituents selected from hydroxyl, halogen, C$_{1-4}$alkyl, C$_{1-4}$alkoxy, C$_{1-4}$alkoxy substituted by 1 to 5 halogen atoms, C$_{3-6}$cycloalkoxy, cyano, phenyloxy, heteroaryl and optionally substituted phenyl;
  and wherein the optionally substituted phenyl or optionally substituted heteroaryl, independently, may be substituted with 1 to 5 substituents selected from hydroxyl, halogen, C$_{1-4}$alkyl, C$_{1-4}$alkyl substituted by 1 to 5 fluorine atoms, C$_{1-4}$alkoxy, C$_{1-4}$alkoxy substituted by 1 to 5 fluorine atoms, cyano and phenyl;
R$_3$ is Z—X$_2$, where Z is CH$_2$, CHF or CF$_2$, and X$_2$ is OH or a residue of formula (a)

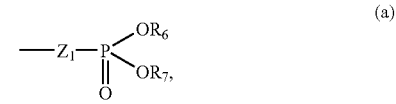

wherein Z$_1$ is a direct bond, CH$_2$, CHF, CF$_2$ or O, and each of R$_6$ and R$_7$, independently, is H, C$_{1-4}$alkyl optionally substituted by 1, 2 or 3 halogen atoms, or benzyl; and
each of R$_4$ and R$_5$, independently, is H or C$_{1-4}$alkyl optionally substituted by 1, 2 or 3 halogen atoms; and
the anellated rings a and b together form 2,6- or 2,7-disubstituted naphthyl, 2,5- or 2,6-disubstituted benzoxazolyl, 2,5- or 2,6-disubstituted benzofuryl, 1,4- or 1,5-disubstituted indolyl, 3,6-indazolyl, or 3,6-N-substituted-indazolyl;
where heteroaryl, where mentioned, refers to a 5-to-8-membered aromatic ring comprising 1 to 4 heteroatoms selected from N, O and S;
in free form or in pharmaceutically-acceptable salt form.

2. A compound according to claim 1, wherein X is O or a direct bond in free form or in pharmaceutically-acceptable salt form.

3. A compound according to claim 1, wherein $R_1$ is $CH_3$ or $CH_2$—OH in free form or in pharmaceutically-acceptable salt form.

4. A compound according to claim 1, wherein $R_2$ is $C_{1-7}$alkyl, substituted $C_{1-7}$alkyl, phenyl, substituted phenyl, phenylalkyl, or substituted phenylalkyl, where the substituents are as defined in claim 1, respectively, in free form or in pharmaceutically-acceptable salt form.

5. A compound according to claim 1, wherein $R_4$ and $R_5$ are hydrogen, in free form or in pharmaceutically-acceptable salt form.

6. A compound according to claim 1 or a pharmaceutically-acceptable salt thereof for use as a pharmaceutical and for use in the preparation of a medicament.

7. A pharmaceutical composition comprising a compound according to claim 1, or a pharmaceutically-acceptable salt thereof in association with a pharmaceutically-acceptable diluent or carrier therefor.

8. A pharmaceutical combination comprising a compound according to claim 1, in free form or in pharmaceutically-acceptable salt form, and one or more members selected from immunosuppressive agents, immunomodulating agents and other anti-inflammatory agents.

9. A compound according to claim 1, that is (R)-2-amino-2-methyl-4-(2-phenyl-benzofuran-5-yl)-butan-1-ol, or a pharmaceutically-acceptable salt thereof.

10. A compound selected from the group consisting of
(R)-2-amino-4-(2-benzo[1,3]dioxol-5-yl-benzoxazol-5-yl)-2-methyl-butan-1-ol,
(R)-2-amino-2-methyl-4-[2-(4-phenoxy-phenyl)-benzoxazol-5-yl]-butan-1-ol,
(R)-2-amino-4-[2-(2,2-difluoro-benzo[1,3]dioxol-5-yl)-benzooxazol-5-yl]-2-methyl-butan-1-ol,
(R)-2-amino-2-methyl-4-[2-(3-phenoxy-phenyl)-benzooxazol-5-yl]-butan-1-ol,
(R)-2-amino-4-[2-(4-cyclopentyloxy-3-methoxy-phenyl)-benzooxazol-5-yl]-2-methyl-butan-1-ol,
2-amino-2-[2-(3-ethyl-1-methyl-1H-indazol-5-yl)-ethyl]propane-1,3-diol,
2-amino-2-[2-(3-heptyl-1-methyl-1H-indazol-5-yl)-ethyl]-propane-1,3-diol and the compound of the formula

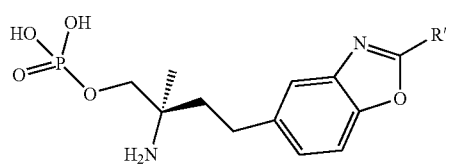

in which R' is of the formula

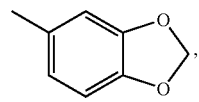

or a pharmaceutically-acceptable salt thereof.

* * * * *